US006876972B1

(12) United States Patent
Kameda

(10) Patent No.: US 6,876,972 B1
(45) Date of Patent: Apr. 5, 2005

(54) SYSTEM FOR AIDING TO MAKE MEDICAL CARE SCHEDULE AND/OR RECORD, PROGRAM STORAGE DEVICE AND COMPUTER DATA SIGNAL EMBODIED IN CARRIER WAVE

(76) Inventor: Toshitada Kameda, No. 929 Higashi-cho, Kamogawa-shi, Chiba-ken (JP)

( * ) Notice: Subject to any disclaimer, the term of this patent is extended or adjusted under 35 U.S.C. 154(b) by 755 days.

(21) Appl. No.: 09/639,645

(22) Filed: Aug. 16, 2000

(30) Foreign Application Priority Data

Aug. 17, 1999 (JP) .......................................... P11-230880

(51) Int. Cl.[7] .............................................. G06F 17/60
(52) U.S. Cl. ........................ 705/3; 705/7; 705/8; 705/9; 345/440; 345/441; 345/442; 345/443; 345/963
(58) Field of Search ................................ 705/2–3, 7–9; 345/440–443, 963; 600/300–301

(56) References Cited

U.S. PATENT DOCUMENTS

| | | | | |
|---|---|---|---|---|
| 4,878,175 A | * | 10/1989 | Norden-Paul et al. .......... | 705/2 |
| 5,072,383 A | | 12/1991 | Brimm et al. ................... | 705/2 |
| 5,247,611 A | * | 9/1993 | Norden-Paul et al. ...... | 715/504 |
| 5,284,152 A | * | 2/1994 | Portnuff et al. .............. | 600/525 |
| 5,325,478 A | | 6/1994 | Shelton et al. ............... | 715/507 |
| 5,361,202 A | * | 11/1994 | Doue ............................. | 705/3 |
| 5,447,164 A | * | 9/1995 | Shaya et al. ................. | 600/523 |
| 5,682,526 A | * | 10/1997 | Smokoff et al. .......... | 707/104.1 |
| 5,788,646 A | * | 8/1998 | Fuchs et al. ................. | 600/523 |
| 5,830,150 A | * | 11/1998 | Palmer et al. ............... | 600/523 |

(Continued)

FOREIGN PATENT DOCUMENTS

| EP | 0 784 283 A1 | 7/1997 | |
|---|---|---|---|
| EP | 784283 A1 | * 7/1997 | ........... G06F/19/00 |
| JP | 4-84945 | 3/1992 | |
| JP | 05-314150 | 11/1993 | |
| JP | 06-030838 | 4/1994 | |
| JP | 08-137946 | 5/1996 | |
| JP | 8-266483 | 10/1996 | |
| JP | 9-147027 | 6/1997 | |
| JP | 09-160965 | 6/1997 | |
| JP | 9-185651 | 7/1997 | |
| JP | 11-134410 | 5/1999 | |
| JP | 11-224238 | 8/1999 | |
| JP | 2000-48093 | 2/2000 | |

OTHER PUBLICATIONS

Baxter–Clinicom linkup pleases nurses, amuses patients, Mar. 21, 1988, National Report on Computers and Health, vol. 9, No. 6, File 636 #01011517.*

Nussbaum, Gerald, Charting vital signs: Computer boost patient care, Aug. 1992, Corporate Computing, vol. 1, No. 2, pp. 203–204, File 149 #01362788.*

Excerpt of Japanese Utility Model Application No. HEI 04–065995, corresponding to Japanase Patent Publication No. 6–30838.

*Primary Examiner*—Joseph Thomas
*Assistant Examiner*—Carolyn Bleck
(74) *Attorney, Agent, or Firm*—Finnegan, Henderson, Farabow, Garrett & Dunner, LLP

(57) ABSTRACT

A system for aiding to make a medical care map includes: a plurality of files for including individual medical care data; a date and time measuring device for measuring a present date and time; a display controlling device for (i) generating main display data to display the medical care data, (ii) selecting one of condition marks set in advance, (iii) generating first sub display data to display the selected condition mark on the care map, (iv) calculating a present position on the care map, and (v) generating second sub display data to display a present mark at the calculated present position on the care map; and a display device for displaying the medical care data on the care map together with the condition mark and the present mark, on the basis of the main display data, the first sub display data and the second sub display data.

23 Claims, 19 Drawing Sheets

U.S. PATENT DOCUMENTS

| | | | | |
|---|---|---|---|---|
| 5,891,049 A | * | 4/1999 | Cyrus et al. | 600/523 |
| 5,913,197 A | * | 6/1999 | Kameda | 705/3 |
| 5,921,920 A | * | 7/1999 | Marshall et al. | 600/300 |
| 5,923,018 A | * | 7/1999 | Kameda et al. | 235/385 |
| 5,936,625 A | | 8/1999 | Kahl et al. | 345/775 |
| 5,956,013 A | * | 9/1999 | Raj et al. | 345/208 |
| 6,321,203 B1 | * | 11/2001 | Kameda | 705/3 |
| 6,322,502 B1 | * | 11/2001 | Schoenberg et al. | 600/300 |

\* cited by examiner

FIG. 2

| | 12-13-94 (Tues) 1st DAY (CCU) | 12-14-94 (Wed) 2nd DAY (CCU) | 12-15-94 (Thur) 3rd DAY (CCU) | ~ | 12-19-94 (Mon) 7th DAY |
|---|---|---|---|---|---|
| RECORD | NURSING SCHEDULE | ↓↓ | | | ↓↓ |
| ACTIVITY RESTRICTION (REST/EXCRETION/CLEANNESS) | BED BATH PUDIC CLEAN ● WASH HELPER | BED BATH PUDIC CLEAN WASH HELPER | BED BATH ○ | | BED BATH ○ |
| MEAL | | MORNING: ○ ● LUNCH: △ ● DINNER: □ | ○ ○ | | ORDINARY MEAL ○ |
| PRACTICE/MONITOR | VITAL SIGN WEIGHT MEASUREMENT SG CATHETER MONITOR CARDIOGRAM PULSE OXIMETER | VITAL SIGN WEIGHT MEASUREMENT | VITAL SIGN WEIGHT MEASUREMENT | | VITAL SIGN WEIGHT MEASUREMENT |
| TEST | CARDIOGRAM BREAST X RAY △ CPK, CPK-MB 24hours FECALURIA | CARDIOGRAM BREAST X RAY CPK, CPK-MB 24hours FECALURIA | CARDIOGRAM ○ BREAST X RAY CPK, CPK-MB ○ 24hours FECALURIA | | CARDIOGRAM ○ BREAST X RAY |
| ORAL MEDICINE/ EXTERNAL MEDICINE | | TIMELY ADMINISTRATION ① | TIMELY ADMINISTRATION ① | | TIMELY ADMINISTRATION ① |
| INJECTION | INSTILLATION | INSTILLATION | INSTILLATION | | ○ |
| TREATMENT | MT EVULSION S-G EVULSION DIV DELETION WRAPPING NEBLIZER SPIRON | A LINE EVULSION B CATH EVULSION NEBLIZER SPIRON | Y-DRAIN EVULSION NEBLIZER SPIRON | | NEBLIZER SPIRON |
| ... | | | | | |

FIG.12

| | March '95<br>2 MONTHS<br>AFTER<br>HOSPITALIZATION | April '95<br>3 MONTHS<br>AFTER<br>HOSPITALIZATION | May '95<br>4 MONTHS<br>AFTER<br>HOSPITALIZATION |
|---|---|---|---|
| MEDICATION | ◉ TIMELY<br>ADMINISTRATION | ☼ TIMELY<br>ADMINISTRATION — 260 | |
| TEST | ◉ March 4th<br>ELECTROCARDIOGRAM<br>◉ March 18th<br>ELECTROCARDIOGRAM<br>201 | ☼ April 15th<br>ELECTROCARDIOGRAM<br>211 | ○ May 15th<br>ELECTROCARDIOGRAM |

March 21
AM10:15

| | ... | 12-13-94 | 12-14-94 | 12-15-94 | | 12-19-94 |
|---|---|---|---|---|---|---|
| ⋮ | ⋮ | ⋮ | ⋮ | ⋮ | | ⋮ |
| TEST | ⋮ | ⬭⬭ | ⬭ | ⬭ | | ⬭⬭ |
| MEDI-CATION | ⋮ | ⬭⬭⬭ | ⬭⬭⬭ | ⬭⬭ | | ⬭⬭ |
| INJECTION | ⋮ | | | | | |
| MEAL | ⋮ | ⬭ | ⬭ | ⬭ | | ⬭ |
| REHABILI-TATION | ⋮ | | | | | |
| ⋮ | ⋮ | ⋮ | ⋮ | ⋮ | | ⋮ |

⬇ THIN OUT EMPTY ROW

| | ... | 12-13-94 | 12-14-94 | 12-15-94 | | 12-19-94 |
|---|---|---|---|---|---|---|
| ⋮ | ⋮ | ⋮ | ⋮ | ⋮ | | ⋮ |
| TEST | ⋮ | ⬭⬭ | ⬭ | ⬭ | | ⬭⬭ |
| MEDI-CATION | ⋮ | ⬭⬭⬭ | ⬭⬭⬭ | ⬭⬭ | | ⬭⬭ |
| MEAL | ⋮ | ⬭ | ⬭ | ⬭ | | ⬭ |
| ⋮ | ⋮ | ⋮ | ⋮ | ⋮ | | ⋮ |

FIG.17

| | BEFORE OPE 12th DAY | ... | BEFORE OPE 2nd DAY | BEFORE OPE 1st DAY | OPERA-TION DAY | ... | AFTER OPE 14th DAY | AFTER OPE 15th DAY | AFTER OPE 16th DAY | ... |
|---|---|---|---|---|---|---|---|---|---|---|
| | 12-1 94' | ... | 12-13 94' | 12-14 94' | 12-15 94' | ... | 12-29 94' | 12-30 94' | 12-31 94' | ... |

FIG.18

| | OUTPATIENT BEFORE | | | HOSPITALIZATION | | | | OUTPATIENT AFTER | | |
|---|---|---|---|---|---|---|---|---|---|---|
| | 12-1 94' | ... | 12-13 94' | 12-14 94' | 12-15 94' | ... | 12-29 94' | 12-30 94' | 12-31 94' | ... |

SYSTEM FOR AIDING TO MAKE MEDICAL CARE SCHEDULE AND/OR RECORD, PROGRAM STORAGE DEVICE AND COMPUTER DATA SIGNAL EMBODIED IN CARRIER WAVE

BACKGROUND OF THE INVENTION

1. Field of the Invention

The present invention generally relates to a new system for aiding or navigating a person related to medical care such as a medical doctor, a nurse, a pharmacist, a medical office worker and so on, to make a medical care schedule and a medical care record. The present invention also relates to a computer readable program storage device and a computer data signal embodiment in a carrier wave, which allow a computer to function as the aiding system.

2. Description of the Related Art

Conventionally, in case that a certain patient comes to a hospital or is brought by an ambulance as an outpatient with a cardinal symptom (i.e., a cardinal symptom of sickness or illness) such as a headache, a sicchasia or vomiturition, a tinnitus, a stomachache and so on, the medical doctor performs an observation or examination for the patient. Then, at first the medical doctor makes up a medical care schedule in his or her mind as for a test, a medical service, an arrangement for hospitalization, a medical operation, an administration of medicine etc., after that in accordance with the observation and the diagnosis. Then, for example, the medical doctor may make such a schedule by writing, on a so-called "instruction table" sheet for exclusive use, the medical care schedule or plan for the patient such as the schedule and content of the test and the medication, the schedule and content of the medical operation, the schedule and content of the post-operation treatment or examination and so on. As for a medical care record for the medical care actions performed on the basis of the schedule, recording by using an electric medical record is becoming widespread in place of a conventional medical record of a paper or sheet.

Recently, as disclosed in Japanese Patent No. 2706645 (Japanese Patent Application Laying Open NO. Hei 9-185651) corresponding to U.S. Pat. No. 5,913,197 and Japanese Patent No. 2815346 (Japanese Patent Application Laying Open NO. Hei 10-214302) corresponding to U.S. Pat. No. 5,923,018 which have been applied by the present inventor, it is also possible to make such a medical care schedule on a table, in which medical care actions of various types are arranged in first rows for each type of the medical care actions and in second rows orthogonal to the first rows for each date, displayed on a computer display. Namely, it is possible to make such a medical care schedule on a medical care schedule table which is displayed by executing a program called as a "care map" (which is a trade mark registered in Japan, and hereinbelow this kind of medical care schedule table is simply referred to as a "care map" as the occasion demands), by filling each item in the care map in accordance with the diagnosis or observation of the medical doctor. More concretely, the medical care schedule maker or recorder such as a medical care doctor sets medical care items related to the pertinent patient as the items to constitute the ordinate (first row) of the table and also sets an appropriate term assigned to the date constituting the abscissa (second row) of the table in which the medical care actions belonging to the set items will be performed, in accordance with the diagnosis or observation, so that the frames of the care map are constructed. Further, he or she inputs the medical care actions to be performed into each frame of the care map at the date and item corresponding thereto (hereinbelow, each frame of the table is called as a "cell" as the occasion demands). Then, after the scheduled medical care action is performed, a performance or result data remains as a confirmed data in each cell of the care map in place of the schedule data. Namely, in this care map, the schedule data is shown with the performance or result record data.

Especially, according to the above mentioned care map, since the hospital concerned personnel such as the medical doctor, the nurse, the pharmacist etc., who actually performs the medical care schedule share the medical care schedule information, it is possible to make the medical care schedule with little loss and perform the medical care schedule while appropriately adjusting or amending it in cooperation with each other e.g., inputting and changing the data associated with each cell (or each item) in the care map at each of the terminals.

However, according to the above mentioned care map, under the actual scene of the recent sophisticated and complicated medical care, the medical care schedule maker or recorder such as a physician in charge etc., may not be a person, who actually performs each medical action (e.g., an assistant physician, a testing doctor or engineer, a pharmacist, a nurse, a rehabilitation engineer, a meal or cocking person and so on), and the communication between them may be often indirectly established by means of a known ordering system using a computer or the like (which is a system to perform the execution command of the medical action through a computer network). Accordingly, there is a problem that it is difficult for the medical care schedule maker or recorder such as a medical doctor to recognize the condition of performance of each medical care action scheduled on the care map e.g., whether or not the medical care action is on a stage of just schedule or on a stage of standing by, whether or not the corresponding order has been issued, whether or not the medical care action is to be performed urgently or at an early date, whether or not the medical care action is to be performed as the occasion demands, whether or not the medical care action has been already performed in line with the schedule, whether or not any result data such as a test result data or the like exists by the execution, whether or not the medical care action has never been performed against the schedule, whether or not the medical care action has been performed somehow against the schedule, whether or not the medical care action to be continuously performed has been actually performed regularly and so on. Namely, there is a problem that it is difficult to rapidly recognize such various conditions on the table or to make the schedule on the table while watching the information indicative of the various conditions on the same table.

Moreover, these various conditions e.g., whether or not the medical care action is to be performed urgently, whether or not the medical care action has been performed in line with the schedule or the like, certainly change by the lapse of time even if no action has been performed. Thus, the operation of inputting the information indicative of those various conditions (e.g., the operation, done by the schedule maker or recorder, of manually inputting the information indicating how the present condition is) requires a large amount of troublesome labors. In addition, the various types of medical care actions have certain mutual relationships (For example, in order to perform one medical care action, another medical action should be performed in advance of that. Or, since one medical care action is performed, another medical care action should be promptly performed after that.). Thus, the operation of inputting the information indicative of those various conditions becomes more difficult since the various conditions are not simply determined by the lapse of time.

Moreover, for example, in case that an emergent patient due to an traffic accident is received or a medical doctor cannot follow his schedule, the medical care action for a patient related to the medical care schedule to be performed very soon may not be actually performed. Further, in such a case, by changing just the date for one item or by changing just the content of the medical care action such as the kind of the medicine rather slightly, the changes as for other large number of items become inevitable in actual cases, so that this problem is very serious. Especially, in a hospital where a large number of serious or urgent patients are accommodated, if such a job or activity to make the medical care schedule or record cannot be speedily performed, it may lead to a fatal event related to a human life. Thus, the veteran or old-professional doctor etc., should spend his or her time and energy in a large amount for the job or activity to change the medical care schedule itself, resulting in that the valuable medical resource runs short corresponding to that amount.

SUMMARY OF THE INVENTION

It is therefore an object of the present invention to provide a system for aiding to make a medical care schedule and/or record, which can aid or navigate the person, who makes up the medical care schedule and/or record such as a medical doctor, a nurse, etc., to make an appropriate medical care schedule and/or record easily and speedily, as well as a program storage device for storing a program such as an information record medium and a computer data signal embodied in a carrier wave, which allow a computer to function as the aiding system.

1) The above object of the present invention can be achieved by a first system for aiding to make a medical care schedule and/or record. The first system is provided with: a plurality of files for respectively including medical care data indicating one of a plurality of types of medical care actions, which are set in advance, in correlation with execution timing data indicating an execution timing of respective one of the medical care actions; a date and time measuring device for measuring a present date and time; a display controlling device for (i) generating main display data to display the medical care data composing one series of medical care schedule for one patient in a format of a table, in which the medical care data are arranged in first rows for each type of the medical care actions and in second rows orthogonal to the first rows for each date, on the basis of the medical care data and the execution timing data included in the files, (ii) selecting one of a plurality of kinds of condition marks set in advance, in correspondence with a relationship between the execution timing of the respective one of the medical care actions and the measured present date and time, (iii) generating first sub display data to display the selected condition mark superimposed on or at the vicinity of the medical care data corresponding to the selected condition mark in the table, (iv) calculating a present position in the table corresponding to the measured present date and time under a condition that a width of one day of the table is converted into 24 hours, and (v) generating second sub display data to display a present mark at the calculated present position; and a display device for displaying the medical care data in the format of the table together with the condition mark and the present mark on the basis of the main display data, the first sub display data and the second sub display data.

According to the first system of the present invention, the files respectively include the medical care data indicating one of a plurality of types of medical care actions in correlation with the execution timing data indicating the execution timing of respective one of the medical care actions. Here, the "medical care data" in the present invention is data indicating one of the medical care actions in various execution conditions such as a medical care action in a condition that the medical care schedule and/or record maker such as a doctor has just made a schedule, a medical care action in a condition that an order related to the scheduled medical care is issued, a medical care action in a condition that it is to be urgently performed, a medical care action which has been already performed, a medical care action to be continuously performed, a medical care action to be intermittently performed during a certain time duration, a medical care action which was scheduled but has never been performed, a medical care action in a condition that it is to be performed as the occasion demand, and so on. On the other hand, the "execution timing data" in the present invention is data indicating an execution timing of the medical care action, such as once, a plurality of times, periodic, continuous, intermit, as the occasion demand, etc., at a certain time point or during a certain time duration. The kinds of the execution timings are arbitrary as long as they can define the condition marks described later in detail. Thus, they are divided into the kinds required to define the condition marks. Also, the execution timing data may be data indicating a time point or a time duration in the past, at the present or in the future, such as a timing when the medical care action has been actually performed (i.e., the execution timing on the past performance base) or a timing when the medical care action is scheduled to be performed (i e., the execution timing on the schedule or plan base).

On the basis of the medical care data and the execution timing data included in the files, the main display data is generated by the display controlling device to display the medical care data composing one series of medical care schedule for one patient in the format of the table, in which the medical care data are arranged in first rows for each type of the medical care actions and in second rows orthogonal to the first rows for each date. Then, the table is displayed by the display device. Here, the "plurality of kinds of medical care actions" in the present invention may be categorized by a hierarchy category system comprising large categories and small categories (normally, each of which corresponds to a name or title itself of the medical care action) belonging to one of the large categories or may be categorized by a non-hierarchy category system. Therefore, a line dividing each medical care action in the table may be a dividing line for each large category. In this case, if there are a plurality of medical care data (of a plurality of small categories), which are to be performed on the same day and belong to the same large category, those are displayed within the same cell of the table. At this time, although the order of the arrangement of the medical care data in the cell is arbitrary, it can be easily seen on the whole if those are arranged in the same order over a plurality of cells corresponding to the same large category striding over a plurality of dates. The "cell" in the present invention is an individual area surrounded by a line dividing each date and a line dividing each type of the medical care action in the table.

On the other hand, a plurality of kinds of condition marks are set in advance, in correspondence with a relationship between the execution timing of the respective one of the medical care actions (which is a time point or time duration in the past, at the present or in the future on the past performance base and the schedule or plane base) and the present date and time, which is measured by the date and time measuring device. Here, the "a plurality of kinds of condition marks" may be a mark indicating that the medical care schedule and/or record maker such as a doctor has just made a schedule, a mark indicating that an order related to the scheduled medical care is issued, a mark indicating that it is to be urgently performed, a mark indicating that the medical care action has been already performed, a mark indicating that the medical care action is to be continuously performed, a mark indicating that a medical care action is to be intermittently performed during a certain time duration, a marks indicating that the medical care action was scheduled but has never been performed, a mark indicating that it is to be performed as the occasion demand, and so on. Further, the condition marks may comprise marks in various shapes, marks in various colors or the combination of those, or may include a line-shaped mark having a length corresponding to the time duration of continuing the medical care action, a mark of a check box type, a meshed marks, an underline mark, a wave-lined mark and so forth. The kinds of the condition marks are arbitrary as long as they can distinguish the various conditions from each other. The visually recognizable marks are preferred as the condition marks.

During the operation of the system of the present invention, when the present date and time is measured by the date and time measuring device, one of the condition marks as described above is selected depending upon the relationship between the execution timing of respective one of the medical care action and the measured present date and time, by the display controlling device such as a CPU (Central Processing Unit). For example, if the present date and time is overlapped on or very close to the scheduled execution timing, an active mark (indicating that the pertinent medical care action is active) is selected. Alternatively, if the present date and time has already passed through the scheduled execution timing, a not performed mark (indicating that the pertinent medical care action has never been performed) is selected. Then, the first sub display data is generated by the display controlling device to display the condition mark selected in this manner, which is superimposed on or is positioned at the vicinity of the corresponding medical care data in the table, so that the condition mark is displayed in the table by the display device. Here, to "superimpose" the condition mark may be to superimpose a half transparent condition mark or a condition mark in a very thin shape with respect to the medical care data which may be text-displayed, or may be to display the condition mark at the background side of the medical care data. In short, to "superimpose" the condition mark means that the display area of the medical care data and the display area of the condition mark are more or less overlapped with each other. By such a condition mark, it is possible to promptly recognize which condition mark corresponds to which medical care data in the table. Further, to display the condition mark "at the vicinity of" the medical care data means to display the condition mark at the up or down, or the left or right side of the medical care data corresponding to the condition mark, at a position closer to it than other medical care data not corresponding to the condition mark (e.g., close enough to visually identify the correspondence between the condition mark and the medical care data).

On the other hand, when the present date and time is measured by the present date and time measuring device, a present position in the table corresponding to the measured present date and time under a condition that a width of one day of the table is converted into 24 hours is calculated by the display controlling device. Then, the second sub display data is generated by the display controlling device to display the present mark at this calculated present position, so that the present mark is displayed in the table by the display device. The second sub display data may be generated such that a mark, which moves in the table by a unit of second, minute, hour or hours in correspondence with the accuracy or frequency of the date and time measurement, is displayed as the "present date and time mark". Further, the shape of the present mark may be a line shaped mark striding over a plurality of cells related to the same date, and such a line shaped mark may be superimposed on the medical care data. Especially, in this case, in order to make the medical care data visually recognizable, it is preferable that a half transparent mark or a mark of dashed or thin line as the present mark is superimposed on the medical care data, or the present mark is superimposed at the background side of the text-displayed medical care data. Alternatively, it is possible to display an island mark (or island marks) such as an arrow as the present mark in the table in place of the line-shaped mark.

As a result, according to the system of the present invention, while displaying the medical care schedule and/or record table, it is possible to easily and promptly recognize in what condition the medical care action displayed as the medical care data is, by virtue of the condition mark and the present mark. Further, since the condition mark is automatically changed along with the elapse of time, it is very convenient because no troublesome resetting operation of the condition information is required. Especially, since it is possible to promptly recognize the fact that the medical care action is now to be urgently performed as the time has elapsed, by virtue of the condition mark and the present mark in the table, it is possible to surely perform this medical care action. It is also possible to promptly recognize the medical care action, which has never been performed against the schedule, by virtue of the condition mark and the present mark in the table.

2) In one aspect of the first system of the present invention, each of the files comprises a first object file for including the medical care data and the execution timing data and further including procedure information, in accordance with which the display controlling device selects one of the condition marks and generates the first sub display data.

According to this aspect, the medical care data and the execution data are taken out of the first object file, so that the main display data is generated by the display controlling device. Further, the procedure information is taken out of the first object file, so that the present date and time is referred to, one of the condition marks is selected, and the first sub display data is generated by the display controlling device, in accordance with this procedure information. Therefore, by using the execution timing data and the procedure data included in the first object file, the first sub display data can be generated efficiently by the object oriented manner.

3) In this aspect, the first object file may further include procedure information, in accordance with which the display controlling device generates the main display data to display the medical care data in respective cells in the table.

By constituting in this manner, the medical care data, the execution timing data and the procedure information are taken out of the first object file, so that the main display data is generated by the display controlling device to display the medical care data in the format of the medical care schedule and/or record table, in accordance with this procedure information. Therefore, by using the medical care data, the execution timing data and the procedure data included in the first object file, the main display data can be generated efficiently by the object oriented manner.

4) In another aspect of the first system of the present invention, the first system is further provided with a second object file for including procedure information, in accordance with which the display controlling device calculates the present position and generates the second sub display data.

According to this aspect, the procedure information is taken out of the second object file, so that the present date and time is referred to, the present date and time position is calculated and the second sub display data is generated by the display controlling device, in accordance with the procedure information. For example, in accordance with the procedure information included in the second object file, the coordinate information prescribing the date field of the table is read out, and the coordinate indicating the present date and time position corresponding to the present date and time in the table is calculated by using this coordinate information as a standard. Therefore, by using the procedure data included in the second object file, the second sub display data can be generated efficiently by the object oriented manner.

5) In another aspect of the first system of the present invention, the display controlling device generates the first sub display data to display the condition mark in one kind if a time interval from the execution timing of the respective one of the medical care actions to the present date and time is longer than a predetermined interval set in advance, generates the first sub display data to display the condition mark in another kind if the time interval is not longer than the predetermined interval, and generates the first sub display data to display the condition mark in further another kind if the present date and time has passed through the execution timing.

According to this aspect, if the time interval from the execution timing of the respective one of the medical care actions to the present date and time is longer than a predetermined interval set in advance (e.g., one day or two days), the first sub display data is generated by the display controlling device to display the condition mark in one kind (e.g., ○ mark indicating "standing by"). If the time interval from the execution timing of the respective one of the medical care actions to the present date and time is shorter than the predetermined interval, the first sub display data is generated by the display controlling device to display the condition mark in another kind (e.g., ◎ mark indicating "being active"). If the measured date and time has passed through the execution timing of the respective one of the medical care actions, the first sub display data is generated by the display controlling device to display the condition mark further in another kind (e.g., × mark indicating "not-performed"). Therefore, it is possible to display the condition mark reflecting the actual condition, which changes depending upon the relationship with the present date and time such as standing by, being active, not performed and so forth, automatically and without delay together with the present mark in the table, which is very convenient.

6) In another aspect of the first system of the present invention, the display controlling device generates the first sub display data to display the condition mark, which extends along the second rows for each date of the table in a length corresponding to a predetermined time duration, if the medical care action corresponding to the condition mark is continuously executed for the predetermined time duration.

According to this aspect, if the medical care action is continuously executed for the predetermined time duration such as a usage of an artificial respirator, the first sub display data to display the condition mark, which extends along the second rows for each date of the table in the length corresponding to the predetermined time duration (e.g., a line shaped mark having a length corresponding to the predetermined time duration), is generated by the display controlling device. Therefore, it is possible to display the condition display mark, which visually expresses the condition of continuous performance, together with the present mark in the table, which is very convenient. The "predetermined time duration" in this aspect may be indicated by the execution timing data, and may be registered for each execution timing data independently (i.e., for each file such as a first object file).

7) In another aspect of the first system of the present invention, the display controlling device selects one of the condition marks differently in accordance with information indicating whether or not the respective one of the medical care actions has been already performed.

According to this aspect, one of the condition marks of various kinds, which vary depending upon whether or not the respective one of the medical care actions has been already performed, is selected by the display controlling device, and is displayed together with the present mark in the table. Whether or not it has been already performed may be determined by referring to flag information, which indicates the case that it has been already performed by "1" (or "0") and the case that it has never been performed yet by "0" (or "1"). Such flag information may be inputted by the inputting device equipped in the system or inputted from another computer or terminal, which is located at another department related to the pertinent execution, through a computer network. Further, such flag information may be registered individually for each file (or for each first object file).

8) In another aspect of the first system of the present invention, the display controlling device selects one of the condition marks differently in accordance with information indicating whether or not an order for the respective one of the medical care actions has been already issued.

According to this aspect, one of the condition marks of various kinds, which vary depending upon whether or not an order for the respective one of the medical care actions has been already issued, is selected by the display controlling device, and is displayed together with the present mark in the table. Whether or not it has been already issued may be determined by referring to flag information, which indicates the case that it has been already issued by "1" (or "0") and the case that it has never been issued yet by "0" (or "1"). Alternatively, by linking an order system with the system of the present invention, the flag information may be automatically inputted each time when the order is issued by the ordering system. Such flag information may be inputted by the inputting device equipped in the system or inputted from another computer or terminal, which is located at another department related to the pertinent order, through a computer network. Further, such flag information may be registered individually for each file (or for each first object file).

9) In another aspect of the first system of the present invention, the display controlling device generates the first sub display data to display the condition mark at a position, which corresponds to the execution timing of the respective one of the medical care actions under the condition that the width of one day of the table is converted into 24 hours, in the table.

According to this aspect, a position, which corresponds to the execution timing of the respective one of the medical care actions under the condition that the width of one day of the table is converted into 24 hours, in the table is obtained by the display controlling device. Then, the first sub display data to display the condition mark at this obtained position such that the condition mark is superimposed on or positioned at the vicinity of the medical care data is generated by the display controlling device. As a result, the table, in which the present mark and the condition mark are displayed respectively at the present date and time position and the position corresponding to the execution timing (date and time) in each cell, can be displayed. Thus, it is possible to easily recognize whether the execution timing is before or after the present date and time on the time axis and whether the execution timing is close to or far from the present date and time, by virtue of the positional relationship between the condition mark and the present mark, which is very convenient.

10) In another aspect of the first system of the present invention, the display controlling device generates the second sub display data to display a line shaped mark, which strides over a plurality of cells corresponding to a same day of the table, as the present mark.

According to this aspect, the second sub display data to display a line shaped mark, which strides over a plurality of cells corresponding to a same day of the table, as the present mark, is generated by the display controlling device. As a result, on the table displayed by the display device, the line shaped present mark is displayed in the cells corresponding to one day and moves along with the elapse of the time (or each time when the display controlling device refers to the date and time measuring device). Thus, it is possible to easily recognize whether the execution timing is before or after the present date and time on the time axis and whether the execution timing is close to or far from the present date and time, by virtue of the positional relationship between the condition mark and the present mark in the cells corresponding to one day, which is very convenient.

11) In another aspect of the first system of the present invention, the first system is further provided with an input device for inputting the medical care data and the execution timing data to the files, the display controlling device generating the main display data and generating the first sub display data and the second sub display data by referring to the measured data and time, each time when the medical care data and the execution timing data are inputted by the input device.

According to this aspect, each time when the medical care data and the execution timing data are inputted (e.g., when inputting new data or changing the content of the existing data) by the input device, the main display data is generated, and the first sub data and the second sub data are generated by referring to the measured present date and time. Thus, even if there is a new input of the medical care data and/or the execution timing data or a change of the content of such data, it is possible to display the table as well as the condition mark and the present mark reflecting the latest medical care data and the latest execution timing data.

12) In another aspect of the first system of the present invention, the display controlling device generates the first sub display data and the second sub display data by periodically referring to the measured data and time.

According to this aspect, the present date and time is referred to by the display controlling device, periodically (e.g., every 10 seconds, every 30 seconds, every minute, every 15 minutes, every 30 minutes, every hour and so on), and the present date and time position is newly calculated on the basis of the new date and time. Further, the condition mark is updated depending upon the relationship between the execution timing and the new present date and time. Then, the first sub display data and the second sub display data are generated, so that the present mark and the condition mark are respectively displayed in the table, on the basis of the latest present date and time. Thus, it is possible to display the condition mark and the present mark appropriately reflecting the actual time or the latest condition.

13) In another aspect of the first system of the present invention, the format of the table has a relative date field using a predetermined reference date as a reference in parallel to an absolute date field, and the display controlling device highlight-displays a portion of the relative date field, which corresponds to the measured present date and time.

According to this aspect, the table displayed by the display device has the relative date field, to which a desired reference data is a reference, in parallel to the absolute date field. Here, the "absolute date field" is a field for a date indicating X year, Y month and Z day. The "relative date field" is a field for a date indicating how may days before or after the reference date such as a date of the medical operation or hospitalization. In the relative date field displayed in this way, the date portion corresponding to the measured present date is highlight-displayed. For example, how many days before or after the date of the medical operation or hospitalization can be promptly understand, which is very convenient. More over, since the portion of the relative date field corresponding to the present date is automatically moved along with the elapse of time, it is not necessary to perform an inputting operation other than specifying the reference date. The "highlight-display" means to display one portion such that a display luminance, a brightness, a chroma, a display method, a font or the like thereof is locally changed to be outstanding in a visual sense.

14) In another aspect of the first system of the present invention, the format of the table has a phase field, which strides over a plurality of dates and is obtained by dividing one series of medical care term for said one patient into different categories set in advance, in parallel to an absolute date field, and the display controlling device highlight-displays a portion of the phase field, which corresponds to the measured present date and time.

According to this aspect, the table displayed by the display device has the phase field obtained by dividing one series of medical care term for one patient into different categories, in parallel to the absolute date field. Here, the "phase" is a term consisting of one day to a plurality of days obtained by dividing one series of medical care term into different categories such as "before hospitalization", "attend as an outpatient", "hospitalization", "intensive care", "rehabilitation", "after hospitalization", and so on. In the phase field displayed in this way, the phase portion corresponding to the measured present date (e.g., the phase of "hospitalization") is highlight-displayed. Thus, it is possible to promptly recognize to which phase the present day belongs, which is very convenient.

15) In another aspect of the first system of the present invention, the format of the table is such a format that each cell is prescribed for respective one of large categories of the medical care actions and that a plurality of the medical care data of a plurality of small categories belonging to one large category are arranged within one cell, the display controlling device generates the main display data to display a plurality of the medical care data of one small category such that the plurality of the medical care data are arranged in one row and stride over a plurality of cells corresponding to said one large category.

According to this aspect, the fields for the types of the medical care actions in the table are divided for each large category, so that each cell is prescribed for each large category. Then, if there are a plurality of medical care data of a plurality of small categories on the same day, which belong to the same large category, those are arranged within the same cell. At this time, a plurality of the medical care data of the same small category are arranged in one row striding over a plurality of cells corresponding to the same large category. Thus, it is possible to easily recognize the presence and absence of the medical care data of the same small category for each date on the whole.

16) In another aspect of the first system of the present invention, the format of the table is such a format that each cell is prescribed for respective one of large categories of the medical care actions and that a plurality of the medical care data of a plurality of small categories belonging to one large category are arranged within one cell, and the display controlling device generates the main display data such that a plurality of the medical care data of one small category are arranged in parallel to each other within one cell if a width of a date field of the table is smaller than a predetermined width and that a plurality of the medical care data of one small category are arranged in serial to each other within one cell if the width of the date field is larger than the predetermined width.

According to this aspect, the medical care data are displayed in the format of the table in which each cell is prescribed for each large category. At this time, the main display data is generated such that, if the width of the date field is smaller than the predetermined width, a plurality of the medical care data of the same small category are arranged in parallel within each cell, and that, if the width of the date field is larger than the predetermined width, a plurality of the medical care data are arranged in series within each call. Thus, it is possible to prevent the degree of overlap of two of medical care data of the same small category in the same cell, from being increased too high (because the width of the date field is too narrow) to easily see those two of the medical care data.

17) In another aspect of the first system of the present invention, the first system is further provided with a specification device for specifying a width of a date field of the table, the display controlling device generating the first sub data and the second sub data by referring to the measured present date and time each time when the width of the date field is changed by the specifying device.

According to this aspect, when the width of the date field is changed by the specifying device, the display controlling device refers to the present date and time again, so as to generate the first sub display data and the second sub display data again. Thus, even if the width of the date field is changed, the present mark can be displayed at an appropriate present date and time position in the table, and the condition mark can be displayed at an appropriate position in the table.

18) In this aspect, the display controlling device may generate the main display data to display at least one portion of the medical care data by an information amount set in advance in correspondence with the specified width when the width of the date field is specified by the specifying device.

By constituting in this manner, each time when the width of the date field is specified by the specifying device, at least one portion of the medical care data by the information amount in correspondence with the specified width is displayed. For example, if the width of the date field or the size of the cell is set small, the characters in the predetermined number of the head portion, the initial or the summary mark of the medical care data is merely displayed. On the other hand, if the width of the date field or the size of the cell is set large, all the medical care data are displayed. Further, if there is an enough space in each cell, data indicating the more detail of the medical care data may be displayed together with the medical care data.

19) In another aspect of the first system of the present invention, each of the files further includes multiple correlation information, which correlates the medical care data with one or a plurality of type fields for the types of the medical care actions of the table while appending a priority order to the medical care data, and the display controlling device selects one of the type fields, to which the medical care data belongs, in accordance with the multiple correlation information and generates the main display data to display the medical care data in the cell corresponding to the selected type field.

According to this aspect, the multiple correlation information, which correlates the medical care data with one or a plurality of type fields of the table with the priority order is included in the file. In operation, one of the type fields of the table is selected by the display controlling device in accordance with the multiple correlation information, and the main display data is generated to display the medical care data within the cell corresponding to the selected type field. Therefore, even if the types of the medical care data and the type fields of the table are not simply one-to-one correspondent with each other, it is possible to assign each medical care data to an appropriate type field as the type field to which the pertinent medical care data substantially belongs. As a result, even if the type fields of the table are freely or roughly set, it is possible to automatically assign each medical care data to a type field directly corresponding to the type of the medical care data, a type field similar to the type of the medical care data or another type field. Thus, since the flexibility and easiness of setting the type fields of the table can be certainly improved, it is practically very convenient.

20) In another aspect of the first system of the present invention, the display controlling device generates the main display data to thin out a type field for the type of the medical care action of the table, which does not correspond to any medical care data to be displayed in the table, from the table.

According to this aspect, in case that there is a type field, which does not correspond to any one of the type fields of the medical care data, (empty cells would be arranged in a row horizontally (or vertically) in the table in correspondence with this type field if this type field is displayed as it is) the main display data is generated by the display controlling device such that this type field is thinned out from the table. Thus, it is possible to prevent the empty cells from being arranged in the table to reduce the effective displayable area in the table and degrade the visibility of the table.

21) In another aspect of the first system of the present invention, the display controlling device generates the main display data to thin out a date field of the table, which does not correspond to any execution timing data, from the table.

According to this aspect, in case that there is a date field, which does not correspond to any one of the execution timing data, (empty cells would be arranged in a row horizontally (or vertically) in the table in correspondence with this date field if this date field is displayed as it is) the main display data is generated by the display controlling device such that this date field is thinned out from the table. Thus, it is possible to prevent the empty cells from being arranged in the table to reduce the effective displayable area in the table and degrade the visibility of the table.

22) In another aspect of the first system of the present invention, the system has two units communicated to each other through a communication line, wherein the files are provided in one of the two units, and the display device is provided in another of the two units.

According to this aspect, the files provided in one of the two units and the display device provided in another of the two units are connected to each other through a communication line, such as a wire line, a wireless line, an exclusive line, a general line, a telephone line and so forth. Thus, by preparing the files in a large sized memory device provide in one unit as a center unit, and by employing such a structure that one or a plurality of other units are arranged as terminal apparatuses, it becomes possible to commonly use or share the same data between the plurality of terminal apparatuses. In addition, the display controlling device may be provided in another of the two units in the same manner as the display device. The date and time measuring device may be provided in either one of the two units.

23) In another aspect of the first system of the present invention, each of the files includes setting procedure information to set at least relative execution timings of the medical care actions composing one series of medical care schedule respectively, in addition to the medical care data and the execution timing data, and in case that the medical care actions composing one series of medical care schedule are specified, the display controlling device sets the execution timings of the specified medical care actions in accordance with the setting procedure information included in the files including the medical care data indicating the specified medical care actions respectively, to thereby update the execution timing data.

According to this aspect, at least relative execution timings of the specified medical care actions are set by the display controlling device, in accordance with the setting procedure information included in the file. When the execution timings are set in this way, the execution timing data are updated and the medical care data are displayed in the format of the table on the basis of the updated execution timing data. Thus, the medical care schedule and/or record maker such as a doctor specifies the medical care actions composing one series of the medical care schedule and/or record, without specifying the execution timings, at least relative execution timings of those medical care actions are automatically set in accordance with the setting procedure information included in the file, so that the table is displayed on the basis of the automatically set execution timings. Therefore, even if a plurality or a large number of medical care actions composes one series of medical care schedule, which are interrelated to each other in complicated manners, the medical care schedule can be constructed in which the before and after relationships or the timing relationships among those medical care actions are appropriately set. Further, even if a plurality of new medical care actions are specified by adding, changing or erasing the medical care action or actions with respect to the medical care actions composing one series of medical care schedule, which has been once constructed, it is possible to automatically set the execution timings of the respective medical acre actions in accordance with the setting procedure information included in the file.

24) The above object of the present invention can be also achieved by a second system for aiding to make a medical care schedule and/or record. The second system is provided with: a plurality of files for respectively including medical care data indicating one of a plurality of types of medical care actions, which are set in advance, in correlation with execution timing data indicating an execution timing of respective one of the medical care actions; a date and time measuring device for measuring a present date and time; a display controlling device for (i) generating main display data to display the medical care data composing one series of medical care schedule for one patient in a format of a table, in which the medical care data are arranged in first rows for each type of the medical care actions and in second rows orthogonal to the first rows for each date, on the basis of the medical care data and the execution timing data included in the files, (ii) selecting one of a plurality of kinds of condition marks set in advance, in correspondence with a relationship between the execution timing of the respective one of the medical care actions and the measured present date and time, and (iii) generating first sub display data to display the selected condition mark superimposed on or at the vicinity of the medical care data corresponding to the selected condition mark in the table, at a position in the table corresponding to the execution timing of respective one of the medical care actions under a condition that a width of one day of the table is converted into 24 hours; and a display device for displaying the medical care data in the format of the table together with the condition mark on the basis of the main display data and the first sub display data to display the selected condition mark superimposed on or at the vicinity of the medical care data corresponding to the selected condition mark in the table, at this obtained position.

According to the second system of the present invention, in the similar manner as the above described first system of the present invention, the main display data and the first sub display data are generated. Especially at this time, the position in the table corresponding to the execution timing of respective one of the medical care actions under a condition that the width of one day of the table is converted into 24 hours is obtained by the display controlling device, so that the first sub display data is generated to display the selected condition mark superimposed on or at the vicinity of the medical care data corresponding to the selected condition mark in the table, at this obtained position. As a result, while displaying the medical care schedule and/or record table, it is possible to easily and speedily recognize in what condition the respective one of the medical care action displayed in the table is by virtue of the condition mark. Further, since the condition mark is automatically changed along with the elapse of time, no troublesome operation of resetting the condition information is necessary, which is very convenient. Especially, since the table is displayed in which the condition mark is displayed at the position corresponding to the execution timing (date and time) in each cell, it is possible to easily and visually recognize whether the execution timing of the medical care action is before or after an arbitrary date on the time axis, whether the execution timing is close to or far from the present date, at which time the medical care action has been performed or to be performed within one day, by comparing the position of the condition mark with the date field, which is very convenient.

In addition, the above described various aspects related to the generation of the main display data and the first sub display date as well as the display of the table and the condition mark in the first system of the present invention may be similarly adapted alone or in combination to the second system of the present invention.

25) The above object of the present invention can be also achieved by a first program storage device readable by a computer. The first program storage device stores a program of instructions to cause the computer to function as at least one portion of the above described first system of the present invention (including its various aspects).

According to the first program storage device, such as a CD-ROM, a ROM, a DVD, a floppy disk or the like, of the present invention, the above described first system of the present invention can be realized as it reads and executes the program of instructions.

26) The above object of the present invention can be also achieved by a second program storage device readable by a computer. The second program storage device stores a program of instructions to cause the computer to function as at least one portion of the above described second system of the present invention (including its various aspects).

According to the second program storage device, such as a CD-ROM, a ROM, a DVD, a floppy disk or the like, of the present invention, the above described second system of the present invention can be realized as it reads and executes the program of instructions.

27) The above object of the present invention can be also achieved by a first computer data signal embodied in a carrier wave and representing a series of instructions for a computer. The series of instructions causes the computer to function as at least one portion of the above described first system of the present invention (including its various aspects).

According to the first computer data signal embodied in the carrier wave of the present invention, as the computer downloads the program in the computer data signal through a computer network or the like, and executes this program, it is possible to realize the above described first system of the present invention.

28) The above object of the present invention can be also achieved by a second computer data signal embodied in a carrier wave and representing a series of instructions for a computer. The series of instructions causes the computer to function as at least one portion of the above described second system of the present invention (including its various aspects).

According to the second computer data signal embodied in the carrier wave of the present invention, as the computer downloads the program in the computer data signal through a computer network or the like, and executes this program, it is possible to realize the above described second system of the present invention.

The nature, utility, and further features of this invention will be more clearly apparent from the following detailed description with respect to preferred embodiments of the invention when read in conjunction with the accompanying drawings briefly described below.

BRIEF DESCRIPTION OF THE DRAWINGS

FIG. 2 is a plan view showing one example of a table which is graphically outputted by the first embodiment;

FIG. 12 is a plan view showing another example of a table which is graphically outputted by the first embodiment;

FIG. 16 is a conceptual diagram of another operation of a system for aiding to make a medical care schedule and/or record as a fifth embodiment of the present invention;

FIG. 17 is a plan view showing one example of a table which is graphically outputted by a sixth embodiment;

FIG. 18 is a plan view showing one example of a table which is graphically outputted by a seventh embodiment;

DETAILED DESCRIPTION OF THE PREFERRED EMBODIMENTS

Referring to the accompanying drawings, embodiments of the present invention will be now explained.

(I) First Embodiment

Figure 1:
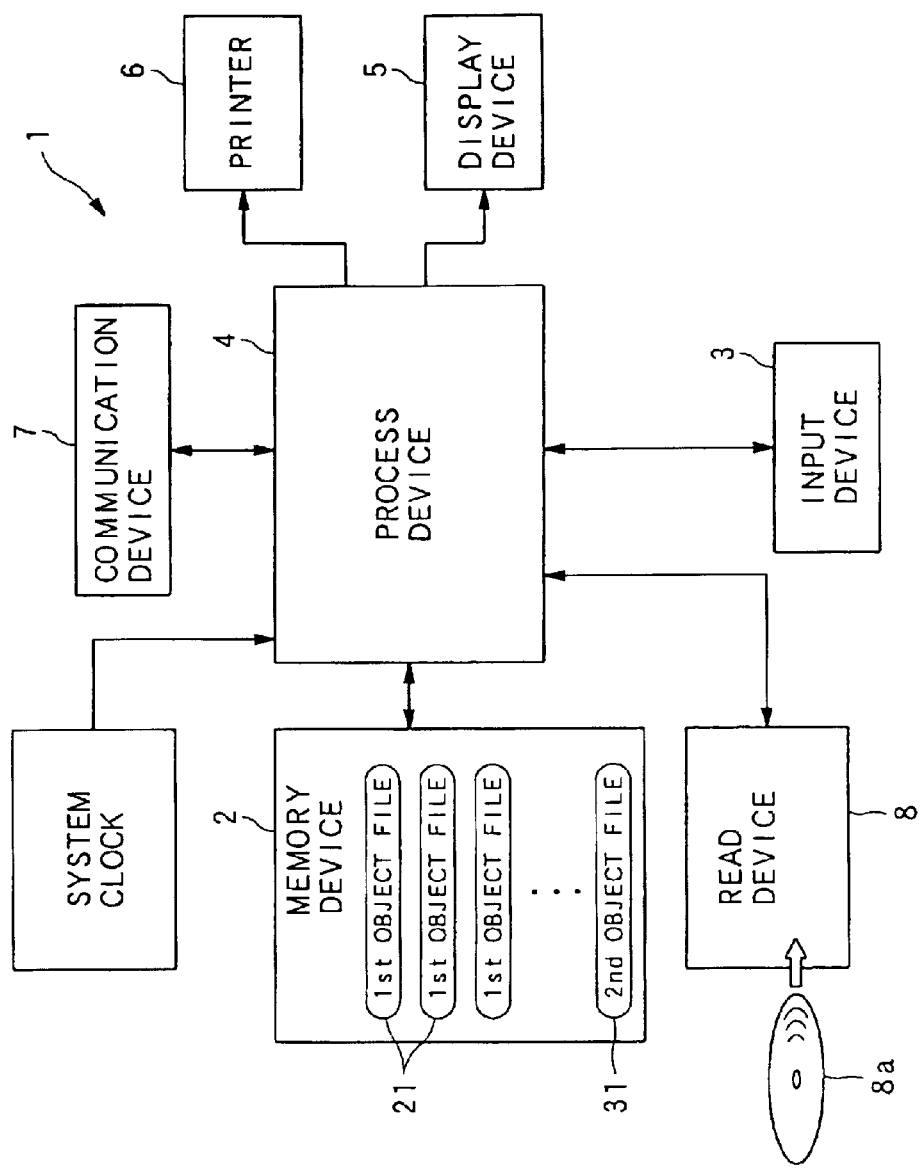
FIG. 1 is a block diagram of a system for aiding to make a medical care schedule and/or record as a first embodiment of the present invention.

FIG. 1 shows a block diagram of a system for aiding to make a medical care schedule and/or record as a first embodiment of the present invention.

In FIG. 1, a system 1 for aiding to make a medical care schedule and/or record may consist of, as a hardware resource, a personal computer, a work station, a middle size computer, a large size computer, a mobile computer (i.e., a hand-carry type information terminal), an electronic diary or the like, and is provided with: a memory device 2; an input device 3; a process device 4; a display device 5; a printer 6; a communication device 7; a read device 8; and a system clock 9.

The memory device 2 is preferably a known large data volume memory device of randomly accessible type, such as a hard disc device, an IC (Integrated Circuit) memory, a magnetic disc device, a magneto-optical disc, an optical disc device or the like.

In the memory device 2, there are constructed a plurality of first object files 21, each including: medical care data indicating either one of a plurality of types of medical care actions, which are set in advance, in association with execution timing data indicating execution timing of respective one of the medical care actions. The first object file 21 further includes procedure information, in accordance with which the process device 4 selects one of a plurality of kinds of condition marks (each of which is a mark to display one of a various conditions set in advance) and generates first sub display data to display the condition mark as described later, in addition to the medical care data and the execution timing data. In the memory device 2, there is also constructed a second object file 31 including procedure information, in accordance with which the process device 4 refers to a present date and time of the system clock 9, calculates a present date and time position in the medical care schedule and/or record table, and generates second sub display data to display a present mark (which is a mark to display a present date and time) as described later. In this manner, the first sub display data and the second sub display data can be generated efficiently by virtue of the object file i.e., by using various procedure information stored in the first object file 21 and the second object file 31, in the present embodiment.

Alternatively, without using the first object file 21 and the second object file 31, those kinds of procedure information may be stored in a program file, which is constituted separately from the medical care data and the execution timing data, and are to be executed as the occasion demand. Also, format information prescribing the frame of the medical care schedule and/or record table among main display data to display the table may be stored in a format information file separately from the first object file 21 and may be read out as the occasion demand, while the procedure information to determine in which cell (surrounded by the frame) the respective medical care data is to be displayed may be stored in the first object file 21.

The input device 3 is provided with a key board, a ten key switch, a mouse, a track ball, an input pen, an input tablet or the like, and is adapted to input the medical care data and the execution timing data as well as other various data or commands, and is further adapted to specify or designate an arbitrary position on the image displayed on the display device 5.

The process device 4 has a CPU (Central Processing Unit), and is constructed to generate the main display data to display the medical care data composing one series of medical care schedule as for one patient in the format of the medical care schedule and/or record in which the medical care data are arranged for each date and for each type on the basis of the medical care data and the execution timing data stored in the first object file 21. Further, the process device 4 is constructed to select one of a plurality of kinds of condition marks set in advance in correspondence with the relationship between the present date and time measured by the system clock 9 and the execution timing of the respective one of the medical care actions, according to the procedure information stored in the first object file 21, and generate the first sub display data to display the selected condition mark such that the selected condition mark is superimposed on or displayed at the vicinity of the corresponding medical care data within the displayed medical care schedule and/or record table. Moreover, the process device 4 is constructed to calculate a present date and time position within the table corresponding to the present date and time measured by the system clock 9, in case that the width of one date in the table is converted into 24 hours, and generate the second sub display data to display the present mark, which is set in advance, at the calculated present date and time position.

The display device 5 may be a known display device such as a CRT (Cathode Ray Tube) display device, an LCD Liquid Crystal Display) device or the like, and is constructed to display the medical care data together with the condition mark and the present mark by the format of the medical care schedule and/or record table, on the basis of the main display date, the first sub display data and the second sub display data generated by the process device 4. Also, the display device is constructed such that an arbitrary position on its picture plane can be designated by the input device 3.

The printer 6 may be a known printer such as a laser beam printer, an ink jet printer or the like, and may be a color type or a black and white type. The printer 6 is constructed to print an arbitrary picture plane displayed on the display device 5 (e.g., the medical care schedule and/or record table) by inputting a predetermined printing command through the input device 3.

The communication device 7 is provided with a modem etc., to perform a data communication of various files including the first object files 21 and data with another computer or the like. The communication device 7 is connected with other large size computer, personal computer, mobile computer (i.e., a hand-carry type information terminal), an electronic diary and the like, through a communication line, such as a wire-line, a wireless-line, an exclusive line, a general line, a telephone line and so on.

The reading device 8 may include a CD-ROM drive, a DVD-ROM drive and an FD (Floppy or Flexible Disk) drive for reading a computer program recorded on a record medium 9, such as a CD-ROM, a DVD-ROM and an FD respectively, for example. The computer program read in this manner allows the computer i.e., the hardware resource of the system 1 to function as the system for aiding to make the medical care schedule and/or record. One or whole portion of the first object files 21 and the second object file 31 constituted in the memory device 2 may be recorded on the record medium 8a, and may be read out as the occasion demand. Especially, it is convenient later to store in advance (i) the first object files 21, which are used for a standard medical care schedule at a stage before making an individual medical care schedule for a specific patient, or (ii) the standard object files 21, from which as the base the individual medical care schedule can be modified or changed, to the record medium 8a together with the computer program since they can be produced at the time of producing the computer program and since their flexibility is high.

The system clock 9 has a calendar function and always measures the present date and time regardless of the on/off of the main power of the system 1. The process device 4 refers to the date and time measured by the system clock 9 when updating the present mark and the condition mark within the medical care schedule and/or record table or at a constant cycle. The system 1 may be constructed such that the process device 4 refers to a present date and time signal of a clock device, which is installed at the external of the system 1 and which outputs the present date and time signal indicative of the present date and time at the constant cycle, in place of the system clock 9, to thereby obtain the present date and time.

Next, one example of the medical care schedule and/or record table, which is displayed on the display device 5 on the basis of the display data generated by the process device 4, is shown in FIG. 2.

As shown in FIG. 2, the medical care data is displayed on the display device 5 by a format of a medical care schedule and/or record table 10, in which date is set on an abscissa 12 (i.e., a horizontal axis) while the type of the medical care action is set on an ordinate 11 (i.e., a vertical axis). In this case, while displaying the table 10, a condition mark 201 indicative of an execution condition of the respective one of the medical care actions is displayed, and also a present mark 202 indicative of a present date and time position under a condition that the width of one day of the date field (i.e., the horizontal axis) is converted into 24 hours is displayed. The condition mark 201 indicates the execution condition as for the medical care data, which is text-displayed and on which the condition mark 201 is superimposed or at the vicinity of which the condition mark 201 is displayed, by the shapes and/or colors thereof.

In the present embodiment, the "types of medical care actions" mainly text-displayed within the table 10 shown in FIG. 2, are the medical care actions categorized in accordance with a hierarchy category system comprising large categories and small categories belonging to each large category. For example, as the large categories, there are "record by doctor or nurse", "process", "injection", "examination", "test", "evaluation", "medication", "meal (food)", "practice", "monitor", "treatment", "activity restriction", "observation", "rehabilitation", "coordination", "hospitalization and leave of hospital", "education for family of patient" and so on. For example, as the small categories belonging to the large category "examination", there are "chest X-ray (photographing)", "head X-ray (photographing)", "electrocardiogram", "body temperature (measurement)", "blood analysis", "urine analysis" and so on.

As shown in FIG. 2, the lines each dividing the types of the medical care actions in the table 10 are lines to divide the large categories such as "examination", "recording" and so on. If there are a plurality of medical care data, which are performed on the same day or belong to the same large category, they are arranged within one cell 10a in the table 10. How to set the column of the types based on the large categories on the ordinate 11 of the table 10 may be fixed or the medical care schedule and/or record maker such as the medical doctor may freely set the column of the types of the table 10 in harmonization with the medical care schedule and/or record for the respective one of the patients.

The "medical care data" which are mainly text-displayed in the table 10 shown in FIG. 2 may be such a medical care action just scheduled by the medical care schedule and/or record maker (e.g., the schedule is still being considered in relation to other patients or other medical care actions constituting the one series of medical care schedule, so that any action other than inputting the information for the pertinent medical care action is not performed yet), may be a medical care action whose order is issued (e.g., an order instructing the medicine distribution or the reservation for a specific examination has been issued to a computer in other departments such as the medicine department or the examination department through the ordering system), may be a medical care action to be urgently performed (e.g., the schedule timing is today or tomorrow), may be a medical care action which has been already performed, may be a medical care action to be continuously performed (e.g., in a condition that the treatment is continuously performed by an artificial respiration device), may be a medical care action to be periodically performed during a predetermined time duration (e.g., in a condition to perform medication 6-times per day continuously for 3 days), may be a medical care action which has been scheduled but has never been performed, may be a medical care action to be performed as the occasion demands (e.g., a specific treatment is to be applied if a certain vital sign exceeds a critical value or a spasm occurs) and so on.

Those kind of medical care data may be inputted one by one for each medical care action composing one series of medical care schedule, so that the first object file 21 may be newly registered or its content may be changed. Those medical care data may be inputted through an input picture plane for the medical care data, which is window-displayed, in a condition that the table 10 is displayed by the display device 5. Those medical care data may be inputted from another system, which is connected to the system 1 by a computer network, through the communication device 7. Alternatively, by an inputting operation through the read device 8 such as the hard disc, the floppy disc or the like, the medical care data related to a plurality of medical care actions composing one series of medical care schedule corresponding to the patient name, the disease name (disease code), the patient attribute (the patient attribute code) and so on may be specified at once.

Then, the "execution timing data" indicative of the execution timing of the medical care action indicated by the medical care data in those kind, is the data indicative of each execution timing (e.g., an execution timing in the past, at the present or in the future, on the result base or on the schedule base) e.g., one time, a plurality of times, periodically, continuously, continually, as the occasion demand and so on. Those kind of execution timing data may be inputted through the input device 3 etc., by directly inputting a certain date and time or a certain period in the same manner as the above mentioned inputting operation for the medical care data. However, in the present embodiment, this inputting operation is advanced such that the execution timing data is registered to the first object file 21 by automatically setting the respective execution timings of the medical care actions composing one series of medical care schedule, with considering the mutual relationships between those medical care actions and by using an appropriate standard date, in accordance with the setting procedure information stored in the first object file 21 as described later.

Figure 3A:
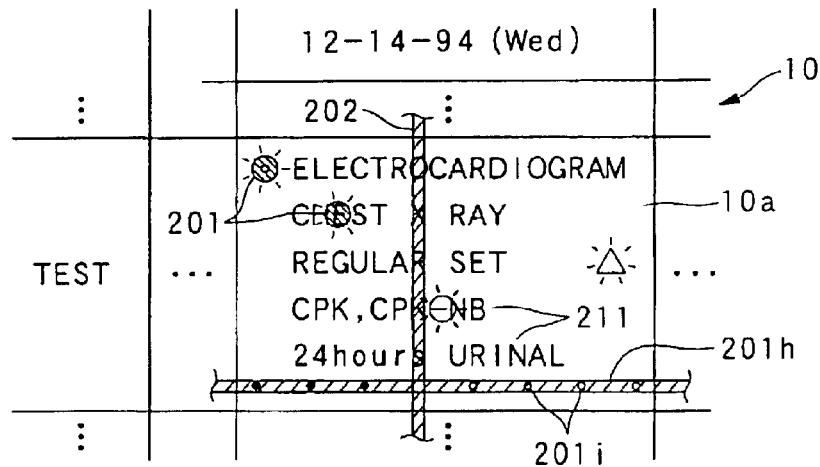
FIG. 3A is an enlarged plan view showing one display form of a portion related to one cell of the medical care schedule and/or record table shown in FIG. 2.
Figure 3B:
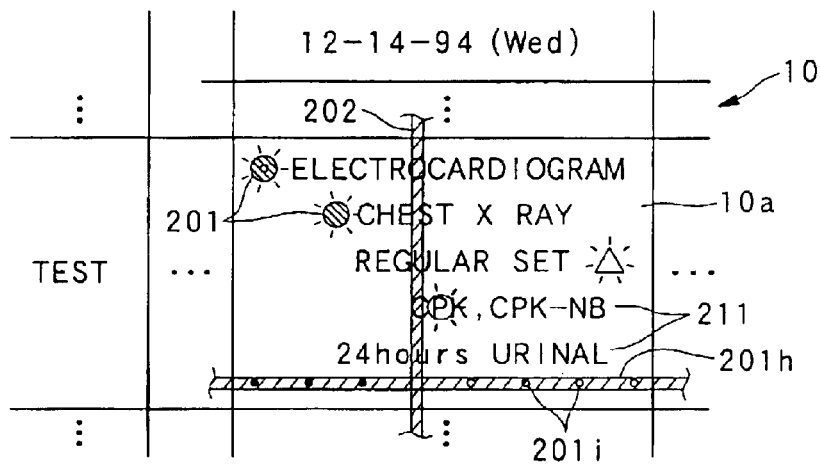
FIG. 3B is an enlarged plan view showing another display form of a portion related to one cell of the medical care schedule and/or record table shown in FIG. 2.
Figure 3C:
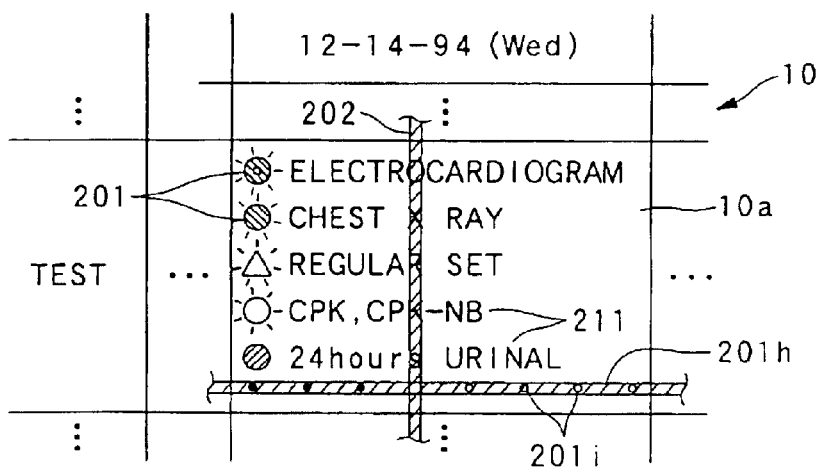
FIG. 3C is an enlarged plan view showing another display form of a portion related to one cell of the medical care schedule and/or record table shown in FIG. 2.

Here, some concrete examples of the medical care data displayed within each cell 10a of the table 10 shown in FIG. 2 as well as the condition mark 201 and the present mark 202 are displayed respectively in FIGS. 3A, 3B and 3C. Here, each of FIG. 3A, FIG. 3B and FIG. 3C is an enlarged view of the portion related to one cell 10a of the table 10 shown in FIG. 2.

In case of displaying the table 10 shown in FIG. 3A, the position corresponding to the execution timing (the date and time) of the respective medical care data 211 within the table 10 under the condition that the width of one day of the table 10 displayed on the display device 5 is converted into 24 hours is obtained by the process device 4. More concretely, the process device 4 obtains the information indicative of the coordinate in the date field from the format information prescribing the date field of the table 10 (i.e., the coordinates corresponding to 0 o'clock and 24 o'clock of a certain date), and calculate the position corresponding to the execution timing (date and time) indicated by the execution timing data related to the condition mark 201 to be displayed under the assumption that each time (each o'clock) corresponds to one $24^{th}$ of those coordinates of the width of one day. As a resolution of such a calculation, one minute, 15 minutes, 1 hour, a plurality of hours or the like may be sufficient. Then, the first sub display data is generated to display the condition mark 201 with superimposing it on the corresponding medical care data 211 or at the vicinity of the corresponding medical care data 211, at this calculated position. As a result, the table 10 is displayed in which the present mark 202 and the condition mark 201 are displayed at the present date and time position and the position corresponding to the execution timing (date and time) respectively within the cell 10a in the table 10. Thus, depending upon whether the condition mark 201 is positioned at a left or right side of the present mark 202, or how distant the condition mark 201 is positioned on the left or right side of the present mark 202, it is possible to easily recognize visually whether the execution timing of each medical care action is before or after the present date and time on the time axis, whether the execution timing is far or close to the present date and time, at about what time of the day each medical care action has been or will be performed and so on.

As shown in FIG. 3B, the display position of each medical care data 211 may be displaced within each cell 10a in correspondence with the execution timing together with the condition mark 201 in the same manner as the arrangement method of the condition mark 201 in the case of FIG. 3A.

Alternatively, as shown in FIG. 3C, the display position of the condition mark 201 and the display position of the medical care data 211 may be fixed in each cell 10a of the table 10 so as to have no relationship with the time as long as they are related to the same date.

However, the method of shifting the condition mark 201 in each cell 10a in correspondence with the execution timing (date and time) and not shifting the medical care data 211 in each cell 10a is advantageous in that the display space can be kept for the medical care data 211 which requires relatively large space since it consists of text data or numerical value data and the like (in contrast, since the condition mark 201 requires a rater small space since it requires a space for just one character, it is advantageous if the display position itself of the condition mark 201 is used as one information indicating the execution timing). Further, the condition mark 201 in the past (i.e., the condition mark 201 displayed on the left side of the present mark 202), whose value as the information indicating the execution time is rather low, may be positioned at a predetermined position at a head (or at a tail) of the medical care data 211 so as to have no relationship with the execution time as shown in FIG. 3C, so that the priority is given to the easy visibility of the medical care data 211.

As shown in FIG. 2 and FIG. 3A to FIG. 3C, as the condition mark 201, there are a mark indicating that the medical care action has been merely scheduled by the medical care schedule and/or record maker, a mark indicating the order corresponding to the scheduled medical care action has been issued, a mark indicating that it is time now to urgently or presently perform the medical care action, a mark indicating that the medical care action has been already performed, a mark indicating that the medical care action is continuously performed, a mark indicating that the medical care action is continually performed within a predetermined time duration, a mark indicating that the medical care action has been scheduled but has never been actually performed, a mark indicating that the medical care action is to be performed as the occasion demand, and so on. In order to indicate the above mentioned various conditions, the marks may comprise marks in different shapes (e.g., ○, ◎, □, △, ☆, ×, etc.,), marks in different colors (e.g., red, blue, yellow, black, bright, dark, etc.,), marks in different shapes and colors in combination, line-shaped marks in different lengths corresponding to the continuous time duration (e.g., extending along the date axis), a mark of check box type, a meshed mark, an underlined mark, a wave-lined marks and so forth. Although those kinds of the condition marks 201 may be arbitrary as ling as they can categorize the various conditions, it is desirable to employ the condition marks 201 which can be easily distinguished from each other visually. It is also desirable that a mark in an outstanding color such as red or orange, or a mark in an outstanding aspect or shape such as a highlighted displayed mark is assigned to a mark indicating the urgency, because of its importance.

Figure 4A:
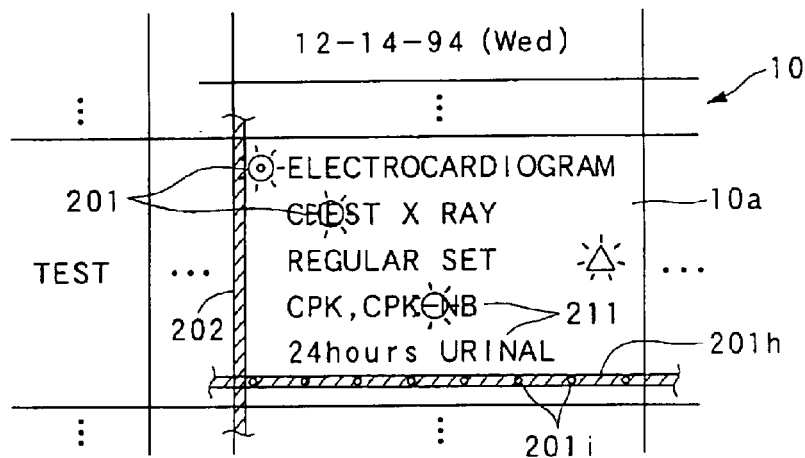
FIG. 4A is an enlarged plan view showing a change of a condition mark in accompaniment with a movement of a present mark on the portion related to one cell of the medical care schedule and/or record table shown in FIG. 2, in an order of FIG. 4A→FIG. 4B→FIG. 4C.
Figure 4B:
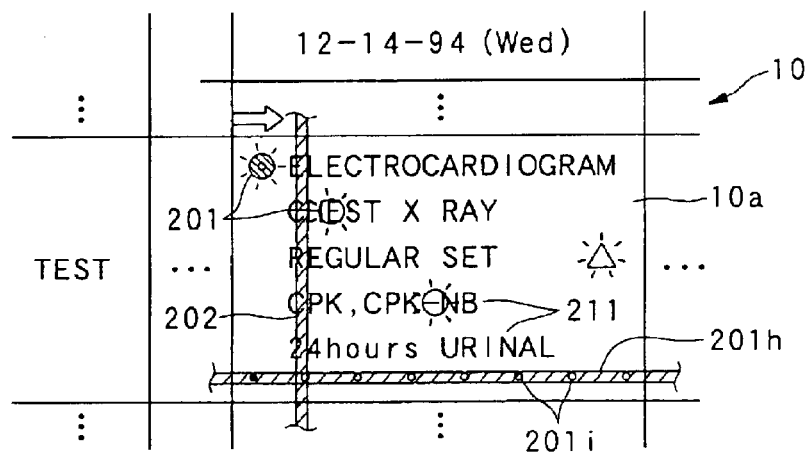
FIG. 4B is an enlarged plan view showing the change of the condition mark in accompaniment with the movement of the present mark.
Figure 4C:
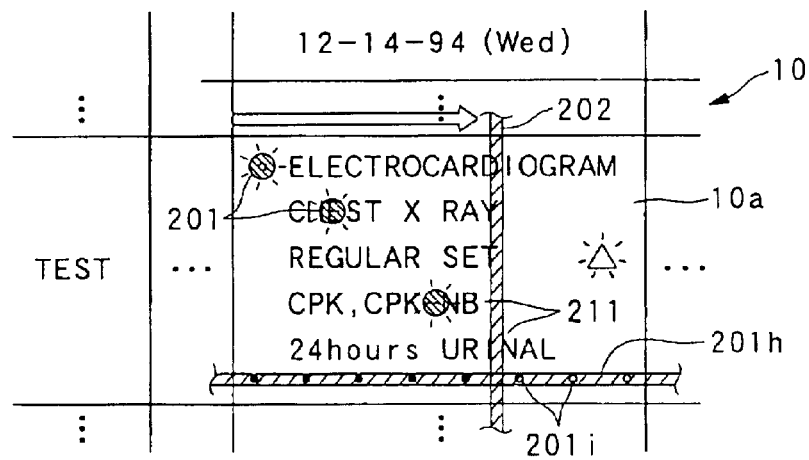
FIG. 4C is an enlarged plan view showing the change of the condition mark in accompaniment with the movement of the present mark.

As shown in FIG. 4.A to FIG. 4C in this order, the present mark 202 is a line shaped mark extending vertically, which moves in the right direction in each figure by the unit of second, minute or hour depending upon the accuracy or frequency of the date and time measurement, as the time elapses. Namely, in this example, as the time elapses, the present mark 202 moves from the present date and time position corresponding to about AM 0:00 o'clock as shown in FIG. 4A, though the present date and time position corresponding to about AM 3:00 o'clock as shown in FIG. 4B to the present date and time position corresponding to about PM 4:00 o'clock as shown in FIG. 4C in the right direction as a result of repeated generation of the second sub display data y the process device 4. The present mark 202 having the line shape in this manner is displayed on the medical care data 211. In order to visually recognize the medical care data 211, it is desirable to superimpose the present mark 202 in a half-transparent manner or in a dashed line on the medical care data 211. Alternatively, it is desirable to display the present mark 202 at the background side of the medical care data 211. Incidentally, as the present mark 202, in place of the line shaped mark, one or plurality of island shaped marks such as an arrow shaped mark ("↓") may be displayed within the table 10.

Figure 5A:
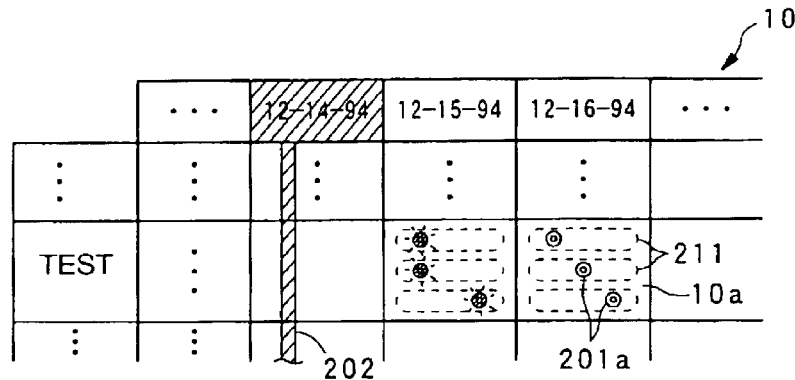
FIG. 5A is an enlarged plan view showing a change of a condition mark in accompaniment with a movement of a present mark on the portion related to one cell of the medical care schedule and/or record table shown in FIG. 2, in an order of FIG. 5A→FIG. 5B.
Figure 5B:
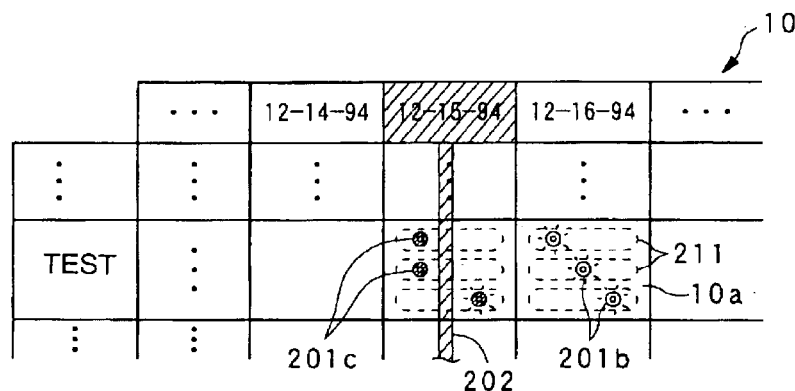
FIG. 5B is an enlarged plan view showing the change of the condition mark in accompaniment with the movement of the present mark.

Especially in the present embodiment, as shown in FIG. 5A, if the time duration from the execution timing of the medical care action to the present date and time exceeds a preset time duration (e.g., 12 hours, 1 day, 2 days), a green ◎ mark 201a indicative of "standing by" for example may be displayed as the condition mark 201 within the table 10 displayed on the display device 5, on the basis of the first sub display data generated by the process device 4. In contrast, as shown in FIG. 5B, if the time duration from the execution timing of the medical care action to the present date and time becomes shorter than this preset time duration as the time elapses, an orange ◎ mark 201b indicative of "active" (in place of the green ◎ mark 201a shown in FIG. 5A) for example may be displayed as the condition mark 201 within the table 10 displayed on the display device 5, on the basis of the first sub display data generated by the process device 4. On the other hand, as shown in FIG. 5B, as the condition mark 201 with respect to which the present date and time measured by the system clock 9 has passed though the execution timing of the medical care action, a purple ⊙ mark 201c indicative of "not-performed" for example may be displayed within the table 10. In contrast, as shown in FIG. 5C, if the medical care schedule and/or maker such as a medical doctor inputs the past performance information, which indicates that the medical care action has been already performed as described layer, for the medical care data which is displayed as the not-performed condition on the table 10, a blown ⊙ mark 201d indicative of "already performed" (in place of the purple ⊙ mark 201c shown in FIG. 5B) for example may be displayed.

Figure 5C:
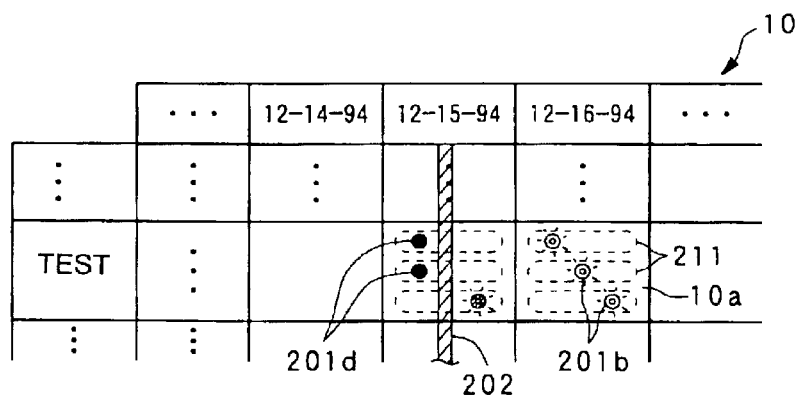
FIG. 5C is an enlarged plan view showing the change of the condition mark after a certain inputting operation is performed in the condition shown in FIG. 5B.

As shown in FIG. 5A to FIG. 5C, it is possible to display in the table 10 the condition mark 201 reflecting the condition change, which changes in relation to the present date and time such as "standing-by", "active", "not-performed", and so on, automatically and without delay by referring to the system clock 9. Incidentally, the preset time duration (e.g., 1 day, 2 days) which becomes the judgment criteria for the active condition or the standing-by condition in this manner may be registered for each first object file 21 (i.e., for each medical care action), may be set for each type of the medical care action, or may be commonly set for all the medical care actions.

From FIG. 2 to FIG. 4C, if the medical care action is continuously performed for a certain time duration such as the usage of the artificial respirator, a line shaped condition mark extending in the left and right direction along the date field in correspondence with this certain time duration may be displayed as the condition mark 201. The certain time duration in this case may be indicated by the execution timing data, and may be registered for each first object file 21. In the same manner, if the medical care action is intermittently performed for a certain time duration (e.g., the medication is performed 6 times per day for 3 days), as shown in FIG. 2 to FIG. 4C, the certain time duration is indicated by a line shaped condition mark 201h, and the scheduled or recorded execution timing at which the medical care action will be or has been intermittently performed may be indicated by a dot mark 201i corresponding to each execution timing on the line shaped condition mark 201h. The color of this dot mark 201i may be changed in relation to the present mark 202 (i.e., in relation to the present date and time).

Especially in the present embodiment, the various condition marks 201 are displayed in the table 10 (refer to FIG. 5C) depending upon the performance record information indicating whether or not the medical care action stored in the first object file 21 has been already performed. In the same manner, the various condition marks 201 are displayed in the table 10 depending upon the order information indicating whether the order corresponding to the medical care action stored in the first object file 21 has been already issued. More concretely, if the order has never been issued, a blue mark is displayed while a light blue mark is displayed if the order has been issued for example. The present embodiment may be constructed such that the ordering system and the system 1 are linked together and that the ordering system is called for and the order is issued for the medical care action designated by the input device 3 on the table 10, by a multiple task while the table 10 is being displayed. By contrasting in this way, when issuing the order, it is possible to automatically input the order information corresponding to the issued order into the first object file 21.

Incidentally, the format information and the program for displaying, which are necessary to display the medical care data by the process device 4 and the display device 5 in the above mentioned manner may be included in a computer program which is stored in a record medium 8a shown in FIG. 1 in advance. The system 1 is constructed to display the table 10 in the format of FIG. 2, in accordance with those format information and program for displaying as well as the procedure information stored in the first object file 21 and the second object file 31 as described later in detail.

Next, the concrete logical structure of the first object files 21, which are logically constituted in the memory device 2, is explained with reference to FIG. 6.

Figure 6:
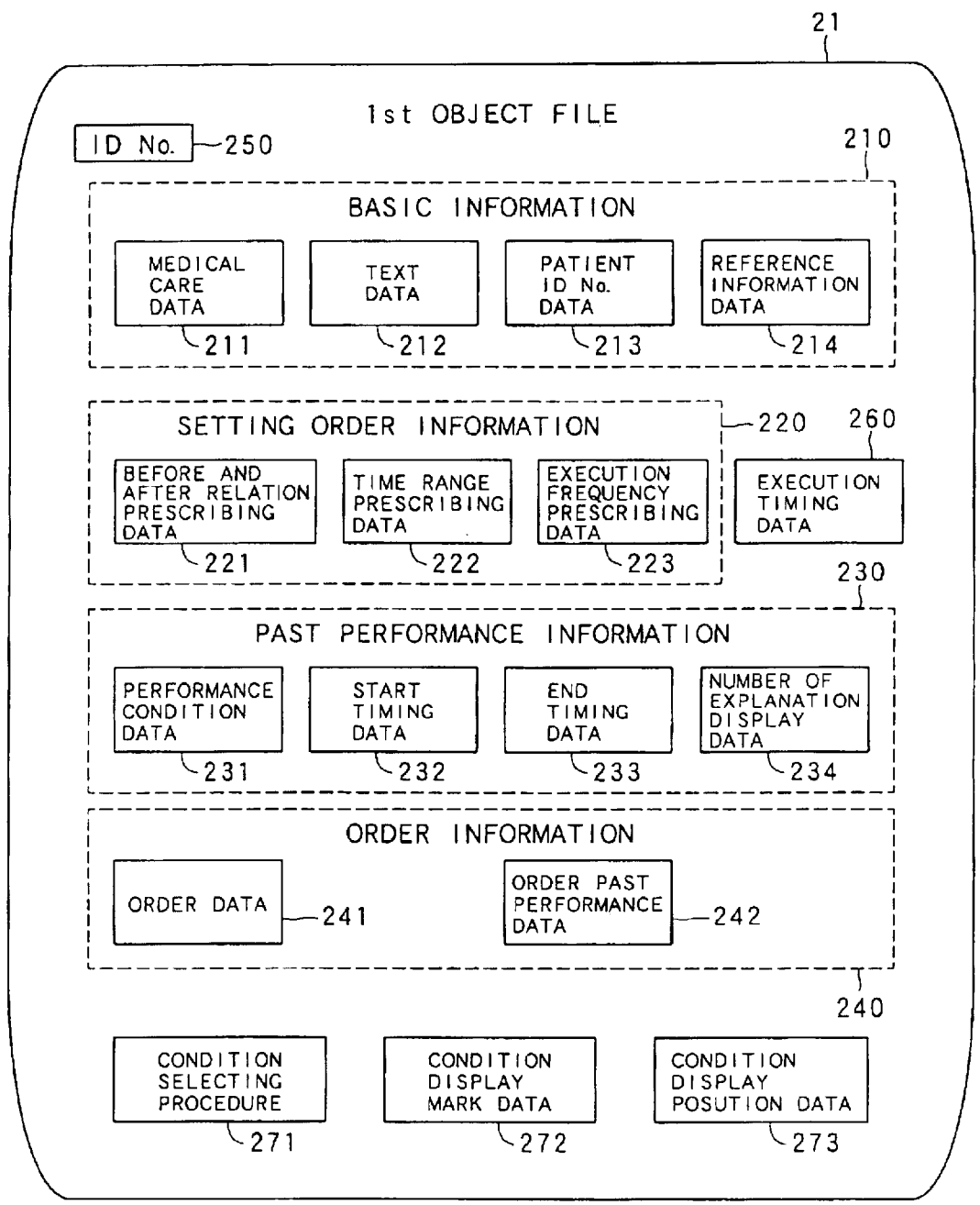
FIG. 6 is a schematic diagram showing a structure of a first object file constituted in the memory device of the first embodiment.

As shown in FIG. 6, the first object file 21 includes basic information 210, which includes aforementioned medical care data 211, and setting order information 220.

At first, the basic information 210 is explained.

In FIG. 6, the basic information 210 includes the medical care data 211 indicating one of the plurality of types of medical care actions set in advance. For example, for each medical care data 211 in the first object file 21, the large category and the small category (which may coincide with the name or title of the medical care action text-displayed as the medical care data within the table 10) belonging to the large category are indicated by using predetermined category codes having a plurality of digits set in advance. As such category codes, category codes which are world-widely or domestically used (e.g., the ICD code, the clinical payment point code) may be adapted, or a category code exclusive for the present invention may be adapted. In summary, as long as the medical care actions are categorized by use of categories suitable for the medical care schedule in the actual and current medical care field, the technical subject of the present invention can be achieved, so that the categorizing method itself is flexible in the present embodiment.

The basic information 210 includes, in addition to the medical care data 211, text data 212, which show a short word or sentence for explaining the detail of the medical care action indicated by the corresponding medical care data 211 to a person who is making the medical care schedule and/or record, and also shows a short word or sentence for explaining the medical care action indicated by the corresponding medical care data 211 to the patient. Further, the basic information 210 includes, in case that the pertinent object file 21 is used as one portion of the medical care schedule and/or record for a specific patient or a virtual patient having a specific disease, (i) a patient ID (Identification) number data 213 indicative of the ID number of the specific or virtual patient and (ii) reference information data 214 related to the medical care data as for the pertinent first object file 21. The reference information data 214 are detailed medical care data accompanying with the medical care action indicated by the medical care data 211 corresponding to each of the first object files 21. For example, the reference information data 214 may be numerical data related to a predetermined type of medical care action such as body temperature data, blood pressure data, concentration data of predetermined component in blood and the like, which are daily measured.

Next, the setting order information 220 is explained. The setting order information 220 is information to respectively set the at least relative execution timings as for the plurality of medical care actions composing one series of medical care schedule. Here, the "relative execution timing" means a timing when one medical care action is to be executed with respect to the execution timing of another medical care action. For example, it indicates that one medical care action is to be executed before or after another medical care action, how many days or hours before, or how many days or hours after another medical care action, or the frequency of the pertinent medical care action.

In FIG. 6, the setting order information 220 includes before and after relation prescribing data 221, which prescribe an at least relative before and after relationship of the execution timing of the medical care action indicated by the medical care data 210 included in the first object file 21 with respect to the end or start of the medical care action indicated by the medical care data 210 included in another object file 21 as a standard. Thus, in the present embodiment, the execution timing of the medical care action indicated by respective one of the medical care data 211 is set by the process device 4 as the occasion demands in accordance with this before and after relation prescribing data 221.

The setting order information 220 includes, in addition to the before and after relation prescribing data 221, time range prescribing data 222, which respectively prescribe a time range in which the medical care action indicated by the medical care data 211 included in the pertinent object file 21 can be executed with respect to the end or start of the medical care action indicated by the medical care data 211 included in another object file 21. Thus, in the present embodiment, the execution timing of the medical care action indicated by respective one of the medical care data 211 is set by the process device 4 as the occasion demands in accordance with this time range prescribing data 222. Further, the setting order information 220 includes, in addition to these before and after relation prescribing data 221 and the time range prescribing data 222, execution frequency prescribing data 223, which respectively prescribe an execution performance frequency of each of the medical care data 211. Thus, in the present embodiment, the execution timing of the medical care action indicated by respective one of the medical care data 211 (e.g., how many times it is executed per day) is set by the process device 4 as the occasion demands in accordance with this execution frequency prescribing data 223.

In FIG. 6, especially in the present embodiment, the first object file 21 further includes past performance information 230. This past performance information 230 is to make the first object file 21, which indicates one medical care action in the medical care schedule, function as a performance record file including the medical care data 211 on the past record base after the medical care action has been actually performed. More concretely, the past performance information 230 includes: past performance condition data 231 of 1 bit indicating whether the medical case action corresponding to the pertinent object file 21 is on the forecast (schedule) base or on the past performance record base; start timing data 232 and end timing data 233 respectively indicating the start timing and the end timing in case that the corresponding medical care action has been actually performed; and number of explanation display data 234 indicating the number of times of the explanation to the patient by use of explanation data for the patient included in the pertinent object file 21.

In FIG. 6, especially in the present embodiment, the first object file 21 includes order information 240. The order information 240 includes order data 241 to make it possible to link the pertinent system for aiding to make the medical care schedule with a known ordering system as explained later. If the order data 241 are described in each of the first object file 21, the order such as an examination reservation, a hospitalization reservation, an operation reservation etc., can be performed in linkage with the medical care action indicated by the medical care data 211 included in each of the first object files 21. Further, the order information 240 includes order past performance data 242 indicating a fact that the corresponding order has been actually performed.

To each of the first object files 21, ID number data 250 having a predetermined digit peculiar to respective one of the object file is given, so that it is possible for the process device 4 in FIG. 1 to search an arbitrary object file 21 by use of the ID number data 250. Further, in case that a new object file 21 is made, new ID number data 250 is given to this new object file 21.

Each of the first object files 21 further includes execution timing data 260. When each execution timing is set by the process device 4 in accordance with the setting order information 220 as a result of designating the medical care actions composing one series of medical care schedule or modifying the medical care schedule, the execution timing data 260 are generated by the process device 4 as data indicating this set execution timing, and are stored in the pertinent first object file 21. Therefore, in case that the pertinent object file 21 does not relate to the setting of the execution timing, this execution timing data may not exist or a predetermined default value may be stored as it. Contrary to this, in case that the execution timing is once set or set again, when the medical care data are to be displayed by using the pertinent object file 21, it is enough to follow the execution timing data 260 as for the execution timing, so that it is not necessary to repeat the same setting operation.

In FIG. 6, the first object file 21 further includes condition selecting procedure information 271, condition mark data 272 and condition display position data 273. The condition selecting procedure information 271 is information to indicate procedures of controlling the process device 4 to refer to the system clock 9 each time when the first object file 21 is updated or periodically to thereby select one of a plurality of kinds of condition marks 201 set in advance, and then calculate a display coordinate corresponding to the execution timing within the table 10, in relation with the execution timing indicated by the execution timing data 260 and the present date and time measured by the system clock 9. The selected newest kind of the condition mark 201 and the calculated display coordinate in the table 10 in accordance with the condition selecting procedure information 271 in this way are stored into the first object file 21 respectively as the condition mark data 272 and the condition display position data 273.

Figure 7:
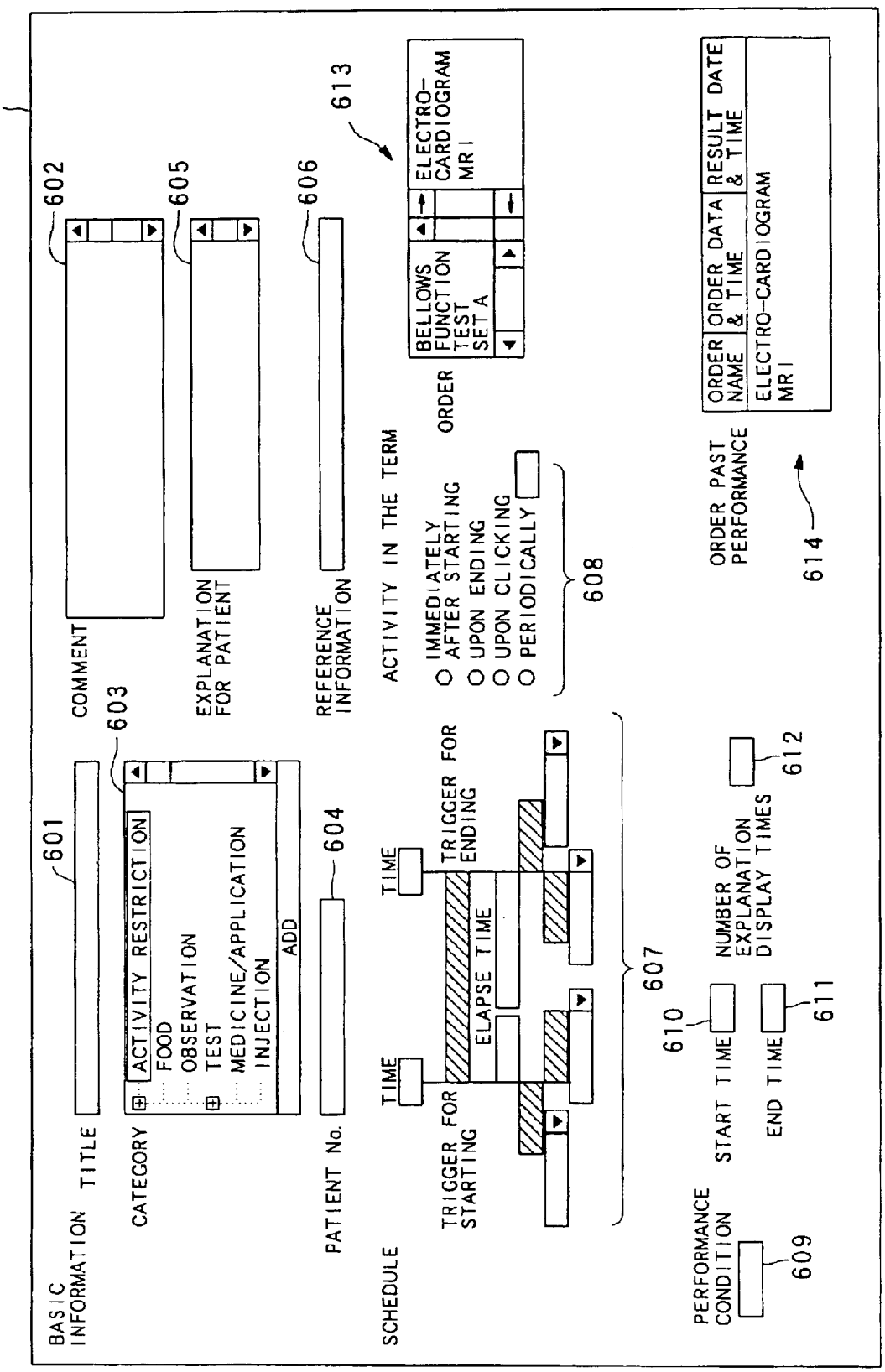
FIG. 7 is a plan view showing an input picture plane when referring to, newly inputting, changing the object file or the like in the first embodiment.

Next, the referring, newly composing and content-changing operations of the first object file 21 including the above described various data are explained with reference to FIG. 6 and FIG. 7. FIG. 7 shows an input picture plane 600, which is displayed on the display device 5 at the time of the referring, newly composing and content changing operations. Text data, numerical data, codes etc., displayed in each field of the input picture plane 600 are composed as a predetermined command is executed by designating a specific medical care action in the table 10 shown in FIG. 2 with a cursor, on the basis of the basic information 210, the setting order information 220, the past performance information 230 and the order information 240 included in the first object file 21 corresponding to this medical care action (refer to FIG. 6).

Especially, the present embodiment is constructed such that the change including newly-inputting and erasing of the data displayed in each field on the input picture plane 600 shown in FIG. 7 can be performed through the input device 3 (refer to FIG. 1).

The medical care action indicated by each of the medical care data 211 which compose one portion of the basic information 210 and are categorized in predetermined codes (refer to FIG. 6) is displayed in a "title" field 601 as text data showing a short word or sentence as the master file stored in advance in the memory device 2 for the code conversion is referred to, for example in FIG. 7. In a "comment" field 602 which is located on a right side thereof, in case that each of the medical care actions cannot be determined only according to the title, the text data showing a short word or sentence for commenting or explaining the content of the medical care action in detail are displayed on the basis of the text data 212 which composes one portion of the basic information 210 (refer to FIG. 6). In a "category" field 603, the categories of the medical care actions are listed up, among which the category corresponding to the medical care action displayed in the "title" field is highlight-displayed. Especially, in the "category" field 603, by the cursor movement by use of the input device 3 etc., various medical care actions which are prepared in a hierarchy manner can be designated, so that it is possible to speedily define an arbitrary medical care action with respect to each the first object files 21. In a "patient number" field 604, in case that the pertinent object file 21 is used when the medical care schedule is to be actually made with respect to a specific patient or a virtual patient having a specific disease, the patient ID number of that specific or virtual patient is displayed on the basis of the patient ID number data 213 composing one portion of the basic information 210 (refer to FIG. 6). Further, in an "comment for the patient" field 605, the text data showing a short word or sentence for commenting or explaining the content of the medical care in an easily understandable manner for the patient are displayed on the basis of the text data 212 composing one portion of the basic information 210 (refer to FIG. 6). In a "reference information" field 606, the existence of the detail information, which can be referred to when each of the first object file 21 is actually used as one portion of the medical care schedule, is displayed by its title, its ID number or the like, on the basis of the reference information data 214 composing one portion of the basic information 210 (refer to FIG. 6).

Therefore, the medical care schedule and/or record maker such as a medical doctor can easily refer to, newly input and change the medical care data, the patient ID number data and so forth by use of each of the fields 601 to 606 based on the various data included in the basic information 210 (refer to FIG. 6), and can easily refer to, newly input and change the text data corresponding to the medical care data.

In FIG. 7, in a "schedule" field 607, a start time of the medical care action indicated by the medical care data 211 included in the pertinent object file 21, a trigger for starting it (e.g., another medical care action related thereto, a start instruction), an end timing, a trigger for ending it (e.g., another medical care action related thereto, an end instruction) and the elapse time are displayed, on the basis of the before and after relation prescribing data 221, the time range prescribing data 222 and the executing frequency prescribing data 223 which compose the setting order information 220 (refer to FIG. 6) as well as the execution timing data 260. In an "activity in the term" field 608, whether the setting process of the execution timing by the process device 4 on the basis of the setting order information 220 included in the pertinent first object file 21 is performed immediately after the start of the medical care action, at an end timing, at time of clicking a predetermined item on the display picture plane of the medical care schedule in the predetermined format described later or periodically executed is displayed by a black circle, on the basis of the before and after relation prescribing data 221, the time range prescribing data 222 and the execution frequency prescribing data 223 (refer to FIG. 6).

Therefore, the medical care schedule and/or record maker such as a medical doctor can easily refer to, newly input and change the before and after relation prescribing data 221, the time range prescribing data 222 and the execution frequency prescribing data 223 by use of each of the field 607 and 608 based on the various data included in the setting order information 220 (refer to FIG. 6). Then, after the setting order information 220 included in each of the first object file 21 is changed, the execution timing is set by the process device 4 in accordance with the setting order information 220 after the change. Thus, the medical care schedule and/or record maker can apply the modification onto the setting order by the process device 4 itself in line with his or her experience and/or favorite. For example, it is possible to apply a modification onto the timing of medicating a specific medicine after a specific medical operation. Incidentally, when the execution timing is set once or set again, the newest execution timing data 260 indicating the set or reset execution timing is stored in the first object file 21. Further, in accordance with the newest execution timing data 260, the start time, the end timing and the like are updated on the input picture plane 600.

In FIG. 7, in a "past performance condition" field 609, whether the medical care action corresponding to the pertinent object file 21 has been already executed or not is shown on the basis of the past performance condition data 231 composing one portion of the past performance information 230 (refer to FIG. 6). In case that the medical care action has been already executed, the start time (which may also include the date) is displayed in the "start time" field 610 on the basis of the start timing data 232 while the end timing (which may also include the date) is displayed in the "end time" field 611 on the basis of the end timing data 233.

Accordingly, the medical care schedule and/or record maker such as a medical doctor can easily input the past performance information by using each of the fields 609 to 611 and can easily search the information later, when the medical care action indicated by the medical care data included in the pertinent object file 21 is executed in an medical care schedule by using the first object files 21.

In an "number of explanation display times" field 612, the number of times that the explanation has been performed with respect to the patient is shown by use of the comment data for the patient included in the first object file 21, on the basis of the number of explanation display data 234 included in the pertinent object file 21 (refer to FIG. 6).

Accordingly, the medical care schedule and/or record maker such as a medical doctor can speedily recognize whether he or she has certainly explained or explained enough to the patient with respect to the same medical care action, just by referring to the "number of explanation display times" field 612 later, after inputting the number of times each time when the explanation is actually made to the patient. In this manner, the present embodiment is convenient from the view point of the informed concept, and is also convenient as a proof showing the fact for the discussion whether it has been really explained or not.

In an "order" field 613, a black circle mark is displayed depending upon whether or not the corresponding order is to be performed on the basis of the order data 241 composing one portion of the order information 240, and an item to be ordered is displayed in case that the order is to be performed. Further, in an "order past performance" field 614, the name of the order which has been actually performed, the date and/or time when each order has been requested, the date and/or time when the order has been performed and the like, are displayed on the basis of the order past performance data 242.

Therefore, the medical care schedule and/or record maker such as a medical doctor can make a good use of the "order" field 613, so as to allow the aiding system 1 of the present embodiment to function as an conventional ordering system, which speeds up starting an operation such as a medicine preparation, an accounting, etc., by promptly sending the information to a terminal device at each division in the hospital. Further, by referring to the "order past performance" field 614, it is possible to easily recognize whether or not each order has been certainly performed.

In the above explanation with reference to FIG. 7, although the basic information 210, the setting order information 220 etc., included in the first object file 21 are newly inputted and changed on the input picture plane 600, at least one portion of these information may be newly inputted and/or changed on the picture plane showing the medical care schedule in the format shown in FIG. 2 other than the input picture plane 600. Further, at least one portion of the information may be newly inputted and/or changed by window-displaying a menu picture plane or the like for inputting and changing the information in the picture plane of the medical care schedule in the format shown in FIG. 2. Even in case that the basic information 210, the setting order information 220 etc., are newly inputted or changed on the picture plane other than the input picture plane 600, the storage content of the first object file 21 is updated. If the input picture plane 600 is displayed after that, the newest various data corresponding to the storage content of the update object file 21 are displayed.

Next, the logical structure of the second object file 31, which is logically constituted in the memory device 2, is explained with reference to FIG. 8.

Figure 8:
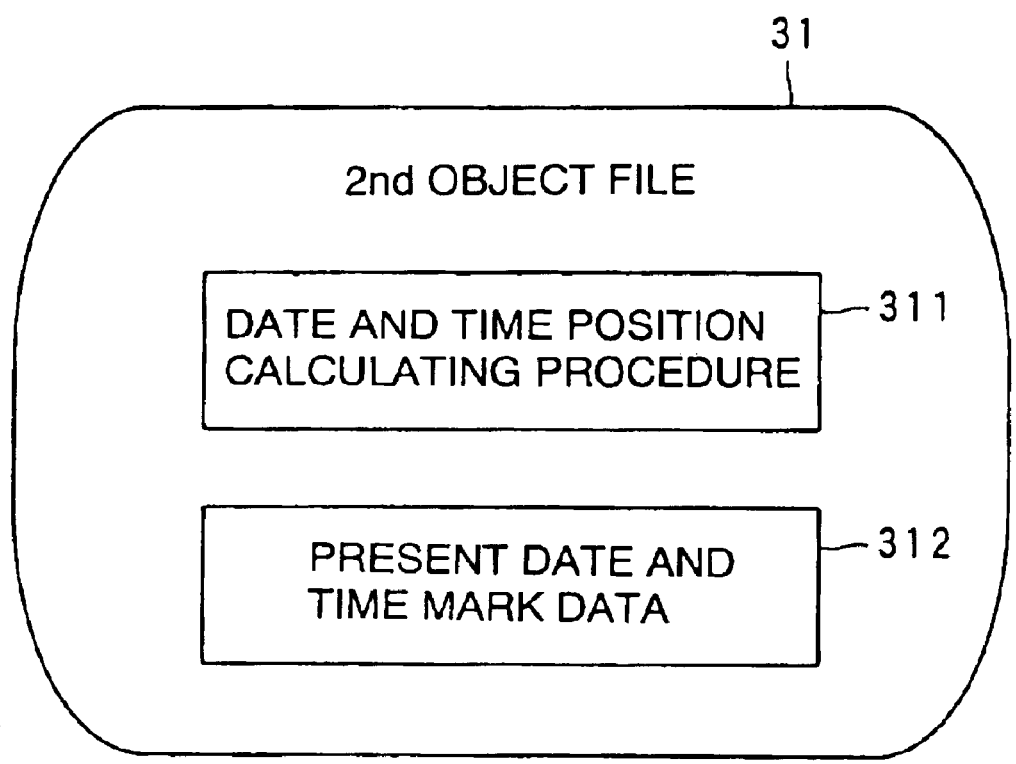
FIG. 8 is a schematic diagram showing a structure of a second object file constituted in the memory device of the first embodiment.

As shown in FIG. 8, the second object file 31 includes: date and time position calculating procedure information 311; and present mark data 312. The date and time position calculating procedure information 311 controls the process device 4 to refer to the system clock 9 each time when the first object file 21 is updated or periodically to thereby calculate the display coordinate of the present date and time position within the table 10, in relation between the present date and time measured by the system clock 9 and the display coordinate of the corresponding date and time in the table 10. On the other hand, the present mark data 312 is data to prescribe the shape of the present mark 202 in the table 10, and may be rewritable so as to display a plurality of kinds of present marks, or may be constituted such that a plurality of present marks are registered in advance and that one of them is selected to be active. Alternatively, the kind of the present mark 202 may be fixed for the sake of simplicity.

Next, the operation of displaying the table 10 in the system 1 is explained with reference to a flowchart of FIG. 9.

Figure 9:
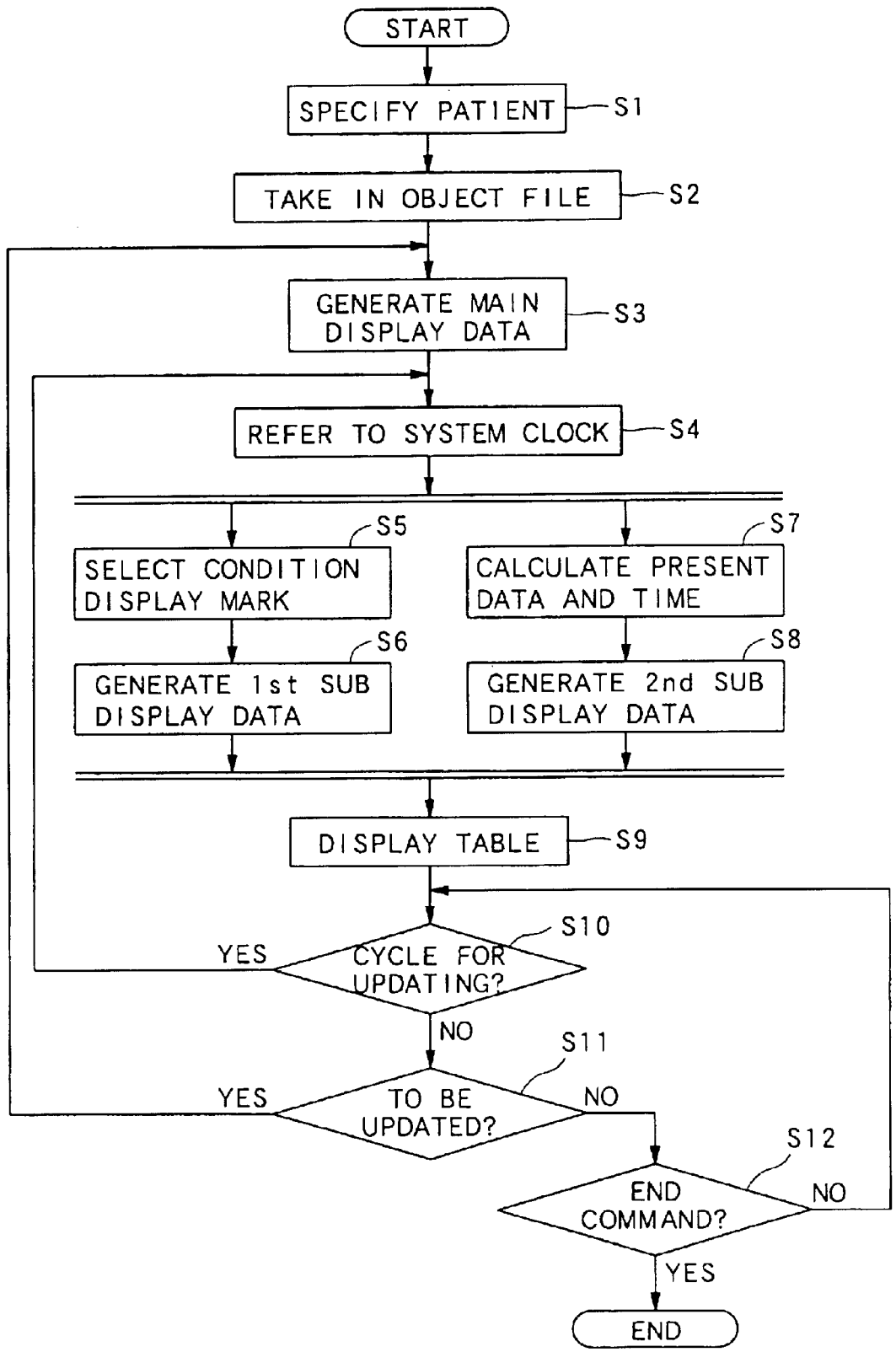
FIG. 9 is a flow chart showing an operation to display the medical care schedule and/or record table in the first embodiment.

In FIG. 9, when the function of displaying the table 10 is activated in the system 1, one patient code related to the table 10 to be displayed is specified by the input device 3 (step S1). The picture plane, on which the table 10 related to a certain patient is called for, may be a list of patients, an electric record or other various picture planes. Then, the first object file 21 is taken in as for the medical care actions composing one series of medical care schedule corresponding to this specified patient, and also the second object file 31 is taken in (step S2). Next, on the basis of the medical care data 211 and the execution timing data 260 stored in the first object file 21 (refer to FIG. 6), the main display data to display the medical care data 211 within each cell 10a of the table 10, whose date field, kind of the medical care actions and frame are prescribed by the format information, are generated by the process device 4 (step S3). Further, in accordance with the condition selecting procedure information 271 stored in the first object file 21 (refer to FIG. 6), the process device 4 refers to the system clock 9 (step S4). Accordingly, the process device 4 selects one of the various condition marks 201 in accordance with the relationship between the present date and time measured by the system clock 9 and the execution timing indicated by the execution timing data 260 in the first object file 21 (refer to FIG. 6) (step S5). For example, if the present date and time is overlapping with the scheduled execution timing or is extremely close to the scheduled execution timing, an "active" mark (i.e., a mark indicating that the pertinent medical care action is to be urgently or presently performed) is selected. Alternatively, if the present date and time has passed through the scheduled execution timing, a "not-performed" mark (i.e., a mark indicating that the scheduled medical care action has never been performed) is selected (refer to FIG. 5B). Then, the first sub display data to display the condition mark 201 selected in this way so that the condition mark 201 is overlapped on or is positioned at the vicinity of the corresponding medical care data 211 in the table 10, is generated by the process device 4. At this time, such a display coordinate that the condition mark 201 is displayed in the cell 10a as shown in FIG. 2, FIG. 3A and FIG. 4A to FIG. 5C, is calculated on the basis of the coordinate of the date field of the table 10 (step S6). Then, the selected condition mark 201 is registered as the latest condition mark 201 to be stored as the condition mark data 272 into the first object file 21 (refer to FIG. 6), and the calculated display coordinate is registered to be stored as the condition display position data 273 into the first object file 21 (refer to FIG. 6).

On the other hand, after the process device 4 refers to the system clock 9 (step S4), in parallel to the above mentioned steps S5 and S6, the process device 4 calculates the present date and time position in the table 10, which corresponds to the measured present date and time under the condition that the width of one day of the table 10 is converted into 24 hours, in accordance with the date and time position calculating procedure information 311 stored in the second object file 31 (refer to FIG. 8) (step S7). Then, in accordance with the present mark data 312 stored in the second object file 31 (refer to FIG. 8), the process device 4 generates the second sub display data to display the present mark 202 as shown in FIG. 2 to FIG. 5C, at this calculated present date and time position (step S8).

Next, the table 10, in which the condition mark 201 and the present position mark 202 as shown in FIG. 2 to FIG. 5C are appended, is displayed by the display device 5 on the basis of the display data in which the first sub display data and the second sub display data are overlapped on the main display data (step S9).

Next, it is monitored whether or not the cycle for updating the present mark 202, which is set in advance, has elapsed by the timer (step S10). At the same time, it is monitored whether or not the present date and time as the standard for the presently displayed table 10 is to be updated, by monitoring the change applied to the presently displayed table 10 (e.g., the change in the size of the date field, the change in the content of the presently displayed medical care data 211) or the enforced input of the update command for the present mark 202 or the condition mark 201 (step S11). If the cycle for updating has elapsed at the step S10 (step S10: YES), the operational flow returns to the step S4, so that the steps from S4 to S9 are repeated to thereby update the first sub display data and the second sub display data. If it is judged to be updated at the step S11 (step S11: YES), the operational flow returns to the step S3, so that the steps from S3 to S9 are repeated to thereby update the main display data, the first sub display data and the second sub display data. On the other hand, during the monitoring process at the steps S10 and S11 (step S10: NO and step S11: NO), it is judged whether or not the command to end the display of the table 10 is inputted (step S12). Then, if the end command is inputted (step S12: YES), one series of the displaying process for the table 10 is ended.

As a result, even if there is no change except for the elapse of the time, the present mark 202 and the condition mark 201 are automatically updated. Further, in case that the medical care data 211 or the execution timing data 260 are inputted (e.g., the new input or the change in the content of the existing data), the medical care data 211 as well as the present mark 202 and the condition mark 201 are updated. As described above, according to the present embodiment, it is possible to display the table 10 with the condition display data 201 and the present date and time data 202 which reflect the latest medical care data 211 and the latest execution timing data 260. In addition, the present date and time measured by the system clock 9 may be an actual present date and time or a virtual present date and time to perform a simulation for the purpose of education or research, in which the elapsing rate of the time is increased as in the case of the fast forward of the video tape or in which the time elapses discontinuously.

In the present embodiment, the first object file 21 stores the setting order information 220 to set the at least relative execution timings of the respective medical care actions composing one series of the medical care schedule (refer to FIG. 6) and the execution timings of the medical care actions are set in accordance with this setting order information 220. Accordingly, it is convenient because the medical care schedule, in which the before and after relationships and the time relationships are appropriately set between the medical care actions, can be made even if the execution timing data 260 is not directly specified by the medical care schedule and/or record maker such as a medical doctor, in such a case that a large number of medical care actions which are complicatedly related to each other constitute one series of the medical care schedule. Further, in such a case that a plurality of medical care actions are newly specified by adding, changing or erasing the medical care action with respect to the medical care actions composing one series of medical care schedule which has been made once, it is very convenient because the execution timings of the medical care actions are automatically set.

The present embodiment may be further constructed to store the data set of a plurality of object files including a plurality of medical care data indicating a plurality of medical care actions composing one series of medical care schedule into the memory device 2 in correlation with the patient code assigned to each individual patient (e.g., a numerical value code in predetermined digits). Alternatively, the present embodiment may be constructed to store each data set into the memory device 2 in correlation with the disease code (e.g., a numerical value code in predetermined digits) assigned to each individual disease among a plural kinds of diseases (e.g., angnapctori, pneumonitis, stomach cancer, cerebral infarction). Alternatively, the present embodiment may be constructed to store each data set into the memory device 2 in correlation with the patient attribute code (e.g., a numerical value code in predetermined digits) assigned to each individual patient attribute in advance including the cardinal symptom (e.g., sex, age, body property, as well as the cardinal symptom). By this, by specifying the patient code, the disease code or the patient attribute code though the input device 3 later on, it is possible to specify the data set corresponding to the specified code, which is convenient. As a result, by making the medical care schedule once as for an arbitrary patient, it is possible to read out the medical care schedule for the patient from the memory device 2 and easily and speedily display it, by designating the patient code, so that the operation of changing the schedule can be also speedily performed. By making the medical care schedule once as for an arbitrary disease, it is possible to read out the medical care schedule for the disease from the memory device 2 and easily and speedily display it, by designating the disease code, so that the operation of changing the schedule can be also speedily performed. Further, by making the medical care schedule once as for an arbitrary patient attribute, it is possible to read out the medical care schedule for the patient attribute from the memory device 2 and easily and speedily display it, by designating the patient attribute code, so that the operation of changing the schedule can be also speedily performed.

The standard medical care schedule corresponding to each disease (each disease code) or the standard medical care schedule corresponding to each patient attribute (each patient attribute code) as described above has a high flexibility as a source for making the medical care schedule for a specific patient. Thus, the data set indicating the standard medical care schedule corresponding to each disease (each disease code) or the standard medical care schedule corresponding to each patient attribute (each patient attribute code) may be stored in advance in the record medium 8a together with the computer program, and may be loaded together when the computer program is loaded. Alternatively, a large number of data sets respectively indicating the standard medical care schedules corresponding to almost all of diseases (almost all of disease codes) and/or the standard medical care schedules corresponding to almost all of patient attributes (almost all of patient attribute codes) mat be stored in advance in a large size memory device equipped in a separate computer system, and the system 1 may download the data set corresponding to a desired disease code or patient code through the communication device 7 (refer to FIG. 1), from this separate computer system having the large size memory device and a communication device.

In the present embodiment, it is preferable that the width of the date field in the table 10 can be freely designated through the input device 3 in the condition that the table 10 is displayed, and that the main display data, the first sub display data and the second sub display data are updated by the process device 4 when the width of the date field is changed by the input device 3 (i.e., the steps S3 to S9 are performed again if the width of the date field is changed since the judgment result at the step S9 is to update them in FIG. 9). By constructing in this manner, it is possible to display the present mark 202 at an appropriate date and time position and display the condition mark 201 at an appropriate position even if the width of the date field is changed. The date field may be changed such that the width of only one portion of the date field is locally changed (i.e., locally expanded) or the width of the date field over the whole table 10 are uniformly changed (in those cases, the portion of the table 10 simultaneously displayed on the display device 5 is changed).

As described above, according to the system 1 of the first embodiment, while displaying the table 10, it is possible to easily and speedily recognize in what condition the medical care data 211 displayed in the table 10 is now, by virtue of the condition mark 201 and the present mark 202. Further, since the condition mark 201 is automatically changed as the time elapses, it is very convenient because a troublesome resetting operation of the condition information is not necessary. Furthermore, since it is possible to promptly recognize a fact that the medical care action is now at the stage to be urgently performed as the time elapses, by the condition mark 201 and the present mark 202 on the table 10, so that it is possible to surely perform this urgent medical care action. Also, it is possible to promptly recognize a medical care action, which has never been performed against the schedule, by the condition mark 201 and the present mark 202 on the table 10. For example, even if the medical doctor etc., has forgotten to perform the scheduled medical care action, it is possible to re-schedule it so as to certainly perform it later on, which is convenient. Further, in case that it is physically impossible to perform all the scheduled medical actions for all the patients because of an appearance of an emergent patient or the like, it is possible to stop performing the medical care action whose importance is relatively low and surely perform the medical care action whose importance is relatively high by watching the table 10, so that it is possible to avoid the worst case while the medical care action, which was scheduled but never been performed, can be certainly performed later by re-scheduling it, which is very convenient.

In the above described embodiment or other embodiments as described below, the medical care data 211 is displayed on the table 10 as the text data as shown in FIG. 2 to FIG. 5C. In place of this or in addition to this, the medical care data 211 may be displayed on the table 10, as abbreviated text data, icon data, graphical mark data (e.g., a mark illustrating "injector" representing the "injection", a mark illustrating "knife" representing the "surgery" and so on), or the combination of those.

(II) Modified Examples of Medical Care Schedule and/or Record Table

Figure 10:
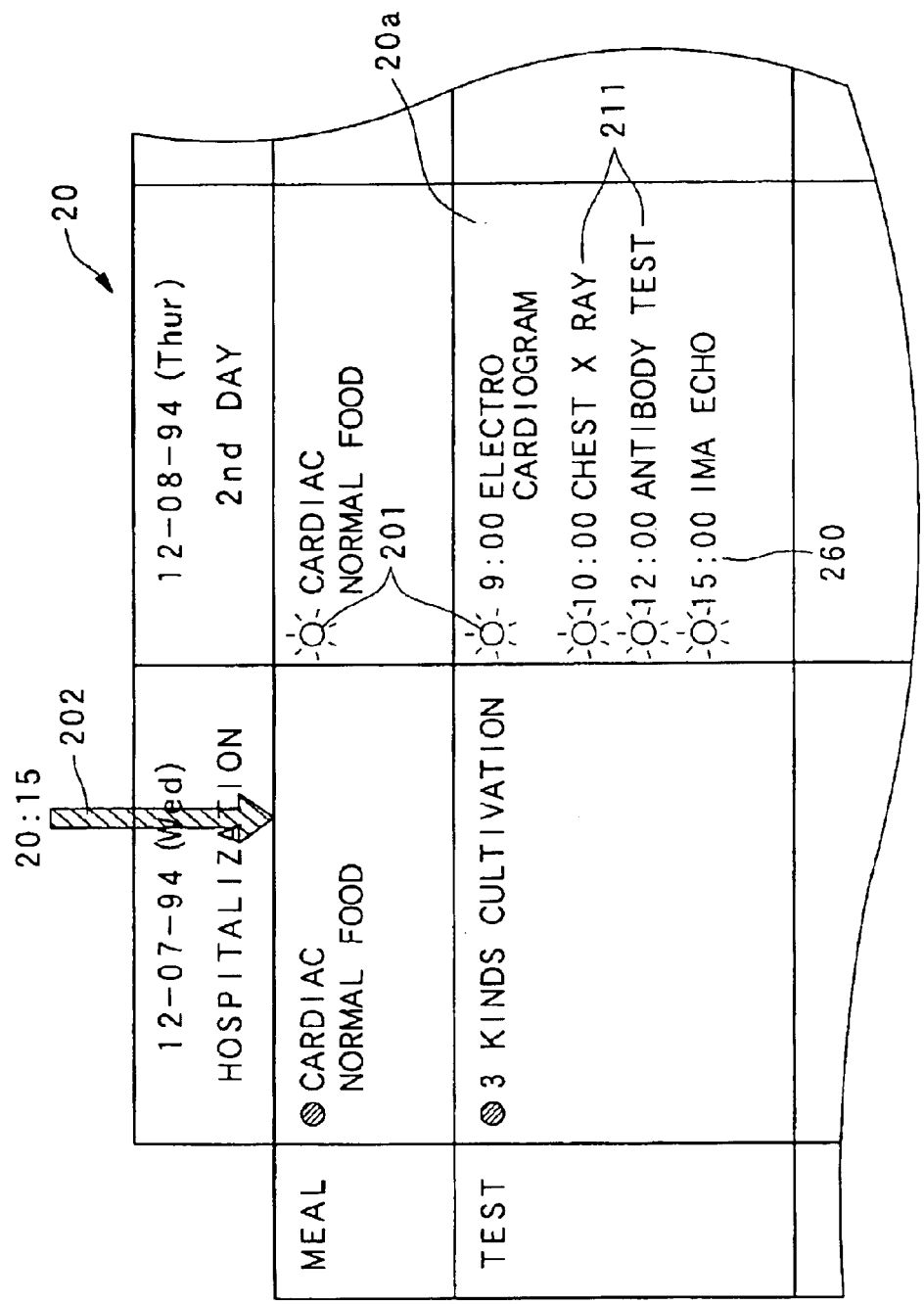
FIG. 10 is a plan view showing another example of a table which is graphically outputted by the first embodiment.

FIG. 10 shows another example of the medical care schedule and/or record table which can be outputted by the display device 5 and the printer 6 in the present embodiment. In this case, a plurality of the medical care data 211 are arranged in the vertical direction for each set time (further, one portion of which is arranged with execution timing data 260) in each cell 20a of a medical care schedule and/or record table 20. The condition mark 201 is displayed adjacent to the medical care data 211, and the present mark 202 having the shape of "↓" is also displayed. Adjacent to the present mark 202, the present date and time ("20:15" in FIG. 10) is also digitally displayed (which is the present time while it is being measured or the latest time when the table 20 is updated).

Figure 11:
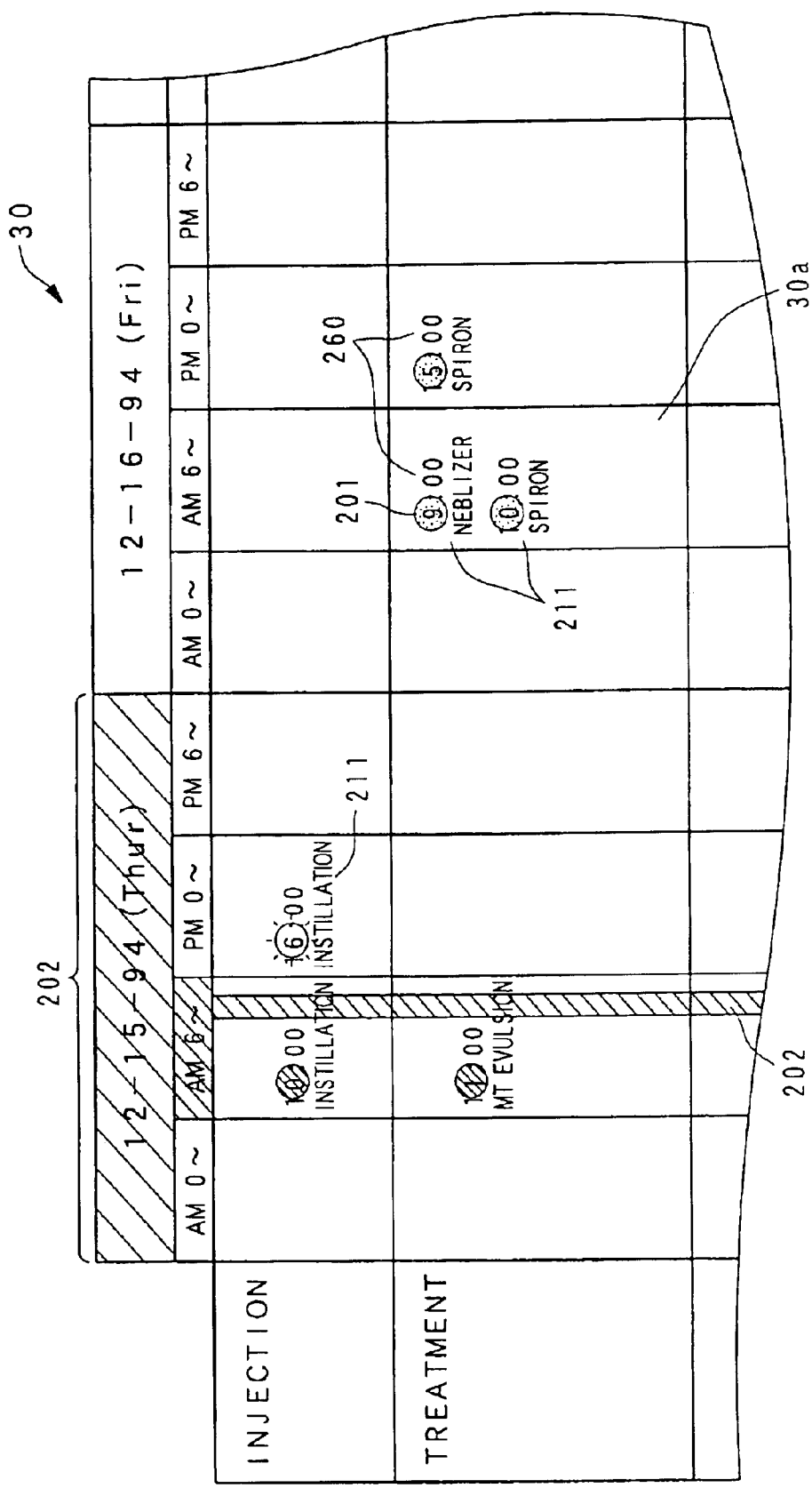
FIG. 11 is a plan view showing another example of a table which is graphically outputted by the first embodiment.

FIG. 11 shows another example of the medical care schedule and/or record table which can be outputted by the display device 5 and the printer 6 in the present embodiment. In this example, the medical care data 211 in a medical care schedule and/or record table 30 is at least partially outputted with being arranged for each predetermined time unit instead of each date. More concretely, the table 30 is outputted in which the medical care actions in each 6 hours are put in one frame of the table and the columns are arranged every 6 hours. Other than 6 hours, although a unit such as 1, 2, 3, 4, 8 or 12 hours which can easily divide 24 hours (one day) can be preferably used here, an arbitrary time unit can be used such that a time unit of long time length may be used with respect to the day time while a time unit of short time length may be used with respect to the night time. In each cell 30a, the medical care data 211 is outputted with being arranged with the execution timing data 260 in the vertical direction for each set time. The condition mark 201 is displayed adjacent to the medical care data 211 (overlapped on the execution timing data 260), and the present mark 202 having the line shape is displayed. The predetermined time duration portion and the present day portion (i.e., the hatched areas) of the table 30 where the present mark 202 is located is highlight-displayed.

FIG. 12 shows another example of the medical care schedule and/or record table which can be outputted by the display device 5 and the printer 6 in the present embodiment. In this case, the medical care data at least partially in a medical care schedule and/or record table 40 are outputted in a format of a table in which the medical care data are integrated by a unit of a plurality of successive dates instead of arranging them for each date. More concretely, the table 40, in which the medical care actions in each one month period are put in one frame 41 of the table and the columns are arranged ever month is outputted. Other than one month, although a time unit such as 3 days, one week, one year or 10 years which are easily understood, can be preferably used here, an arbitrary time unit can be used such that a short time length may be used for the time unit with respect to the period of the hospitalization while a long time length may be used for the time unit with respect to the period for the outpatient. The condition mark 201 is displayed adjacent to the medical care data 211 and the execution timing data 260 (only the portion indicative of the month and date), and the present mark 202 having the line shape is displayed. Adjacent to the present mark 202, the present date and time ("March 21 AM10:15" in FIG. 10) is also digitally displayed (which is the present time while it is being measured or the latest time when the table 20 is updated).

Figure 13:
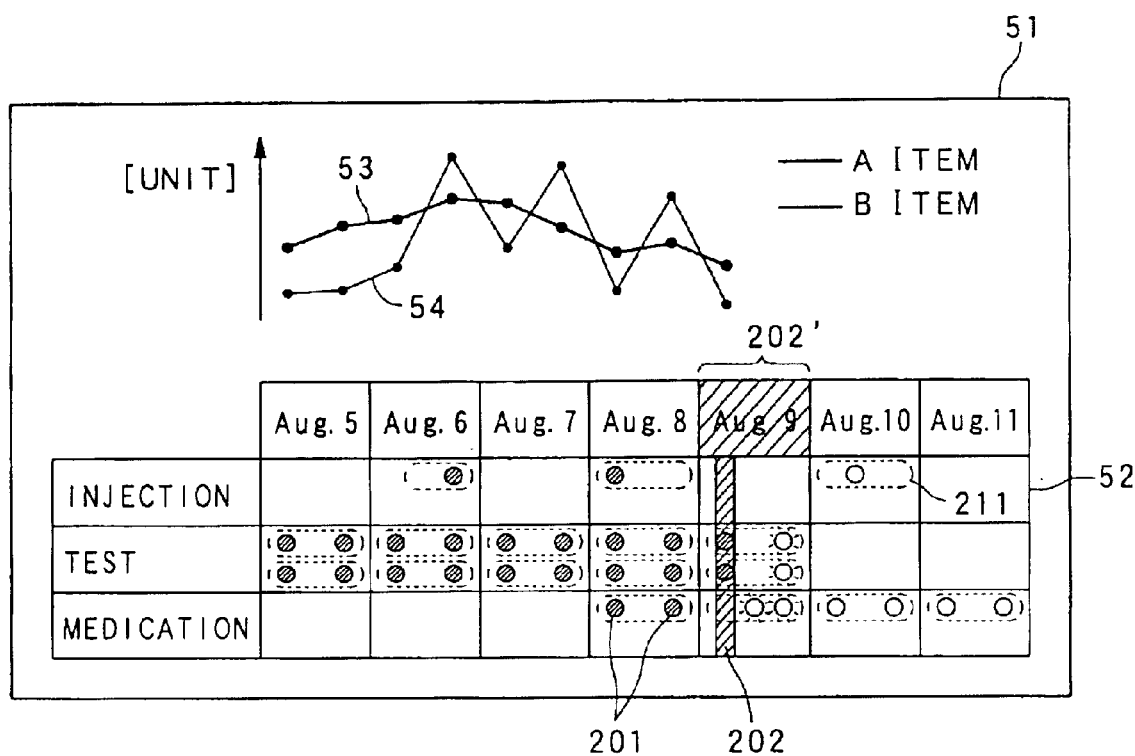
FIG. 13 is a plan view showing another example of a table which is graphically outputted by the first embodiment.

FIG. 13 shows another example of the medical care schedule and/or record table which can be outputted by the display device 5 and the printer 6 in the present embodiment. In this case, the reference information data 214 (refer to FIG. 6), which indicate the detail of the predetermined medical care action, such as numerical data related to a certain medical care action which is repeatedly recorded with respect to a plurality of dates (e.g. the body temperature data, the blood pressure data, the specific content concentration in the blood data measured for each day), are correlated with the medical care data 211. Then, a medical care schedule and/or record table 52 is displayed at one portion of the picture plane 51 of the display device 5 and at the same time the numerical data is displayed as a graph having the abscissa corresponding to the arrangement of the dates of the table 52 at another portion of the picture plane 51. Namely, as shown in FIG. 13, the table 52 is displayed in the lower portion of the picture plane 51 while a polygonal line graph 53 indicating the numerical data as for the A item (e.g. the body temperature) and the polygonal line graph 54 indicating the numerical data as for the B item (e.g. blood pressure), each of which have the time axis of the date of the table 52, are displayed in the upper margin of the table 52. The condition mark 201 is displayed adjacent to the medical care data 211 or overlapped on the medical care data 211 in each cell 52a, and the present mark 202 having the line shape is displayed. The present day portion (i.e., the hatched area) of the table 30 where the present mark 202 is located is highlight-displayed.

The above explained modified examples of the medical care schedule table can be applied to not only the first embodiment but also other embodiments described below.

(III) Second Embodiment

The second embodiment of the present invention is explained with reference to FIG. 1 to FIG. 4C and FIG. 9.

The first embodiment is constructed such that the condition mark 201 and the present mark 202 are displayed in the table 10 as shown in FIG. 1, FIG. 2 and FIG. 9. In contrast, as shown in FIG. 3A, FIG. 3B and FIG. 4, the condition mark 201 is displayed at the position corresponding to the execution timing of the medical care action under the condition that the width of one day of the date field is converted into 24 hours, while the present mark 202 is not displayed in the second embodiment. Namely, the medical care schedule and/or record system of the second embodiment is constructed such that the second object file 31 is omitted in the hardware structure of the first embodiment shown in FIG. 1, and the processes to display the present mark 202 (i.e., the steps S7 and S8) are omitted in the software structure of the first embodiment shown in FIG. 9. Other structures of the second embodiment are the same as those of the first embodiment.

By constructing in this manner, although the second embodiment is inconvenient in that the present mark 202 cannot be seen as compared with the first embodiment, the second embodiment can maintain the convenience that the condition mark 201 to display the condition of the performance which is different in relation to the present date and time can be seen on the table 10 while promoting the simplicity of the hardware and software structures as compared with the first embodiment.

In addition, it is possible that the present mark 202 is not displayed but the portion corresponding to the present date of the date field is highlight-displayed as in the case of the modified examples shown in FIG. 11 or FIG. 13, so that the position of the present date is clear on the table 10.

(IV) Third Embodiment

The third embodiment of the present invention is explained with reference to FIG. 1, FIG. 2 and FIG. 9.

The first embodiment is constructed such that the main display data, the first sub display data and the second sub display data are updated by the process device 4 if it is judged that the present date and time as a standard is to be updated in the condition that the table 10 is displayed as shown in FIG. 1, FIG. 2 and FIG. 9 (refer to the step S11 in FIG. 9). In contrast, in the third embodiment, when the width of the date field is specified (e.g., changed or initially set) by the input device 3, the main display data is generated such that at least one portion of the medical care data 211 is displayed in the information amount corresponding to the specified width. For example, if the size of the cell 10*a* or the width of the date field is set small, the main display data is generated to display only the predetermined number of the head portion or the initial of the medical care data 211, or display only the summary mark or the icon indicative of the medical care data 211. If the size of the cell 10*a* or the width of the date field is set large, the main display data is generated to display all the medical care data 211. Or, if it is judged that there is an enough space within each cell 10*a*, the main display data is generated to display the more detailed information related to the medical care data 211 together with the medical care data 211. Further, the system may be constructed such that the detailed items related to the medical care data 211 (e.g., the reference data 214 as shown in FIG. 6) are automatically appeared in the table 10 if the width of the date field is increased to be wider than a preset width. Namely, the medical care schedule and/or record system of the third embodiment is constructed such that the hardware structure thereof is the same as that of the first embodiment shown in FIG. 1, and the software structure thereof is the same as that of the first embodiment as shown in FIG. 9 except that, in the process of generating the main display data (i.e., in the step S3), the main display data is generated to display the medical care data 211 in the information amount corresponding to the width of each cell 10*a* (i.e., the main display data is generated after the information amount of display is determined depending upon the result of comparison between the width of each cell 10*a* and the standard width). Other structures of the third embodiment are the same as those of the first embodiment.

As for the size change of the width of the date field or the cell 10*a*, it is essentially enough to adjust the font size of the medical care data 211 to be displayed. However, as in the third embodiment, it is advantageous to adjust the information amount of the medical are data 211 displayed in the cell 10*a* in order to maintain the visual easiness of the table, since the medical care data 211 can be displayed in the cell 10*a* by using the font size in a certain range.

(V) Fourth Embodiment

Figure 14:
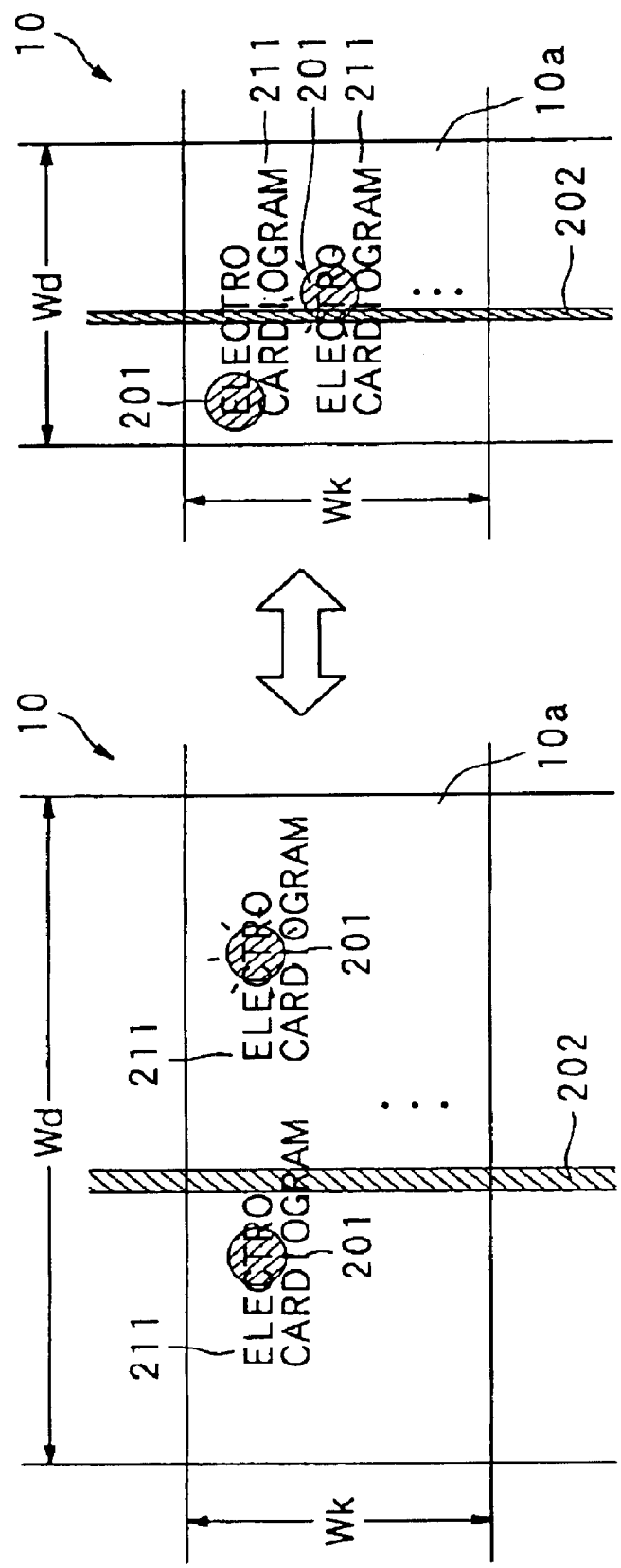
FIG. 14 is a conceptual diagram enlarging and showing a portion related to one cell of the medical care schedule and/or record table displayed by a system for aiding to make a medical care schedule and/or record as a fourth embodiment of the present invention.

The fourth embodiment of the present invention is explained with reference to FIG. 1, FIG. 2, FIG. 9 and FIG. 14. FIG. 14 shows a portion of one cell 10*a* of the table 10, which is displayed by a medical care schedule and/or record system of the fourth embodiment.

The first embodiment is constructed such that the table 10 is displayed in the format that each cell 10*a* is prescribed for each large category of the medical care action and a plurality of the medical care data 211 of the small categories belonging to one large category are arranged in one cell 10*a* as shown in FIG. 1, FIG. 2 and FIG. 9. In contrast, in the fourth embodiment, if a width Wd of the date field is smaller than a predetermined width, the process device 4 generates the main display data to display a plurality of the medical care data 211 of the same small category (i.e., the same name or title) arranged in parallel in each cell 10*a* (refer to a right half portion of FIG. 14). On the other hand, if the width Wd of the date field is not smaller than the predetermined width, the process device 4 generates the main display data to display a plurality of the medical care data 211 of the same small category (i.e., the same name or title) arranged in series in each cell 10*a* (refer to a left half portion of FIG. 14). Namely, the medical care schedule and/or record system of the fourth embodiment is constructed such that the hardware structure thereof is the same as that of the first embodiment shown in FIG. 1, and the software structure thereof is the same as that of the first embodiment as shown in FIG. 9 except that, in the process of generating the main display data (i.e., in the step S3), the main display data is generated after judging a plurality of the medical care data 211 of the same small category are to be arranged in parallel or in series in each cell 10*a* in correspondence with the width Wd of each cell 10*a* (e.g., after judging it by comparing the width Wd of each cell 10*a* with a reference width Wref set in advance). Then, with respect to a height Wk of each cell 10*a*, the change is applied so that a plurality of medical care data 211 of the same small category can be within the cell 10*a* even if they are arranged in parallel. Further, the calculation of the positions of the present mark 202 and the condition mark 201 by using the width Wd of the cell 10*a* after the change as a standard is performed. Other structures of the fourth embodiment are the same as those of the first embodiment.

Therefore, according to the fourth embodiment, it is possible to prevent such a situation from being generated that two the medical care data 211 of the same small category are difficult to see on the table 10 since they are overlapped with each other severely as a result of the small width Wd of the date field. Further, it is possible to prevent the space in the cell 10*a* from being abused because two medical care data 211 of the same small category are arranged in parallel although the width Wd of the date field is large enough.

In the above described first to fourth embodiments, a plurality of medical care data of the same small category are generated in such a format that they are arranged in one horizontal row over a plurality of cells 10*a* corresponding to the same large category. In other words, even if there are no medical care data of the same small category within the same cell 10*a*, as long as there are a plurality of medical care data of a plurality of small categories belonging to the same large category in the cells 10*a*, which are adjacent to each other or which are at least within the same table and which correspond to different dates, the vertical position of the medical care data of each small category within the cell 10*a* is maintained at a constant position (e.g., one horizontal row over a plurality of cells 10*a* are exclusively assigned to the medical care action of the same small category on the whole). By constituting in this manner, it is possible to easily recognize the presence or absence of the medical care action of the same small category for each date visually on the whole. However, a process of thinning out such an exclusive horizontal row where the medical care data hardly exists (i.e., a process of assigning the medical care data of the small category to another horizontal row for another category or somewhere nearby as an exceptional occasion) may be performed.

Further, in the above described first to fourth embodiments, a plurality of medical care data of the same small category within the same cell 10*a* may be displayed such that they are overlapped with each other in series (i.e., positioned on the same horizontal row) while shifting them by an amount corresponding to the difference in the execution timings of the corresponding medical care actions. By constituting in this manner, if the width of each cell 10*a* in the table 10 is relatively small as compared with the display width of two or more medical care data of the same small category displayed in the same cell 10*a*, those two or more medical care data have a relatively high degree of overlapping. On the contrary, if the width of each cell 10*a* in the table 10 is relatively large as compared with the display width of two or more medical care data of the same small category displayed in the same cell 10*a*, those two or more medical care data have a relatively low degree of overlapping. Therefore, in order to make those medical care data able to see easily, the width of each cell 10*a* may be enlarged by using the input device 3 in correspondence with the degree of overlapping which depends on the shortness in time therebetween.

(VI) Fifth Embodiment

Figure 15:
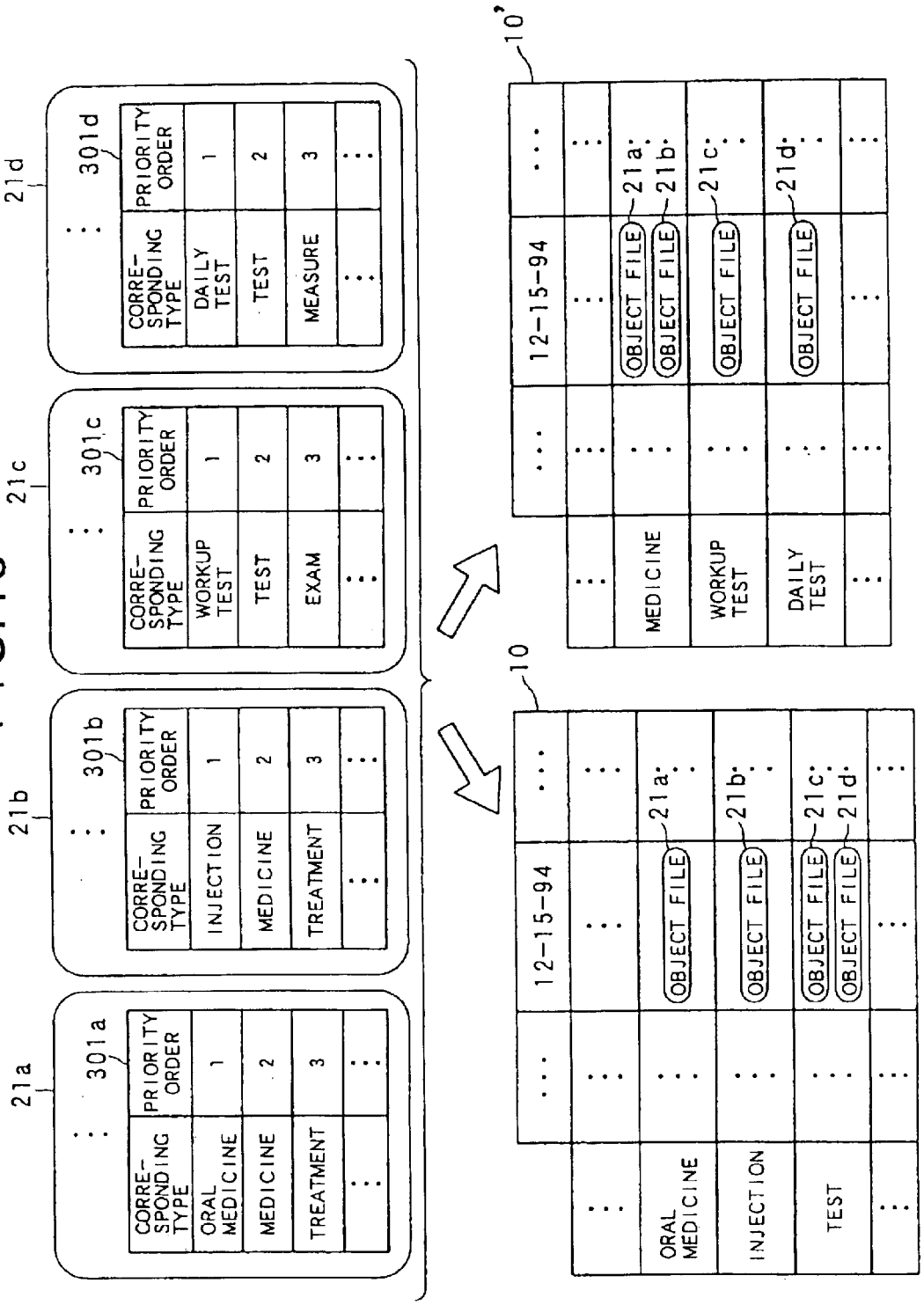
FIG. 15 is a conceptional diagram of one operation of a system for aiding to make a medical care schedule and/or record as a fifth embodiment of the present invention.

A fifth embodiment of the present invention is explained with reference to FIG. 15 and FIG. 16. FIG. 15 shows one operation of the fifth embodiment. FIG. 16 shows another operation of the fifth embodiment.

In the above first to fourth embodiments, it is sometimes difficult to categorize the type of the medical care action. Namely, one action may be categorized into either one of a type A and a type B. Further, one action may be categorized into a type A and may be categorized into a type A', which includes the type A or is included in the type A, depending upon the types composing the medical care schedule and/or record table, which may be set as a default one or which may be selected or modified by the medical care schedule and/or record maker.

Therefore, in the fourth embodiment, as shown in an upper portion of FIG. 15, the first object files 21*a*, 21*b*, 21*c*, 21*d*, . . . have multiple correlation information 301*a*, 301*b*, 301*c*, 301*d*, . . . , respectively. Thus, depending on the types present in the table 10 shown in FIG. 2, each of the first object files 21*a*, 21*b*, 21*c*, 21*d*, . . . finds out to which type the pertinent object file itself is to be corresponding, with referring to the corresponding type data and the priority order data in each multiple correlation information 301. For example, as shown in the upper portion of FIG. 15, the multiple correlation information 301*a* of the first object file 21*a* has the corresponding type data and the priority order data indicating that the object file 301*a* is to belong to the type "oral medicine" with the highest priority (priority No. 1), is to belong to the type "medicine" with the second priority (priority No. 2), is to belong to the type "treatment" with the third priority (priority No. 3) and so on. The multiple correlation information 301*b* of the first object file 21*b* has the corresponding type data and the priority order data indicating that the object file 301*b* is to belong to the type "injection" with the highest priority, is to belong to the type "medicine" with the second priority, is to belong to the type "treatment" with the third priority and so on. The multiple correlation information 301*c* of the first object file 21*c* has the corresponding type data and the priority order data indicating that the object file 301*c* is to belong to the type "workup test" with the highest priority, is to belong to the type "test" with the second priority, is to belong to the type "examination" with the third priority and so on. The multiple correlation information 301*d* of the first object file 21*d* has the corresponding type data and the priority order data indicating that the object file 301*d* is to belong to the type "daily test" with the highest priority, is to belong to the type "test" with the second priority, is to belong to the type "measure" with the third priority and so on.

Accordingly, in case that a medical care schedule table 10 shown in a lower left portion of FIG. 15 is currently displayed, i.e., the types "oral medicine", "injection" and "test" are present in the type column of the medical care schedule table 10, the first object file 21*a* is correlated with the "oral medicine" type according to the priority order data of the multiple correlation information 301*a* (indicating that the highest priority is given to the "oral medicine"). In this case, the first object file 21*b* is correlated with the "injection" type according to the priority order data of the multiple correlation information 301*b* (indicating that the highest priority is given to the "injection"). In this case, the first object file 21*c* is correlated with the "test" type according to the priority order data of the multiple correlation information 301*c* (indicating that the second priority is given to the "test") while the "workup test" type to which the highest priority is given by the multiple correlation information 301*c* is not present in the table 10. Further in this case, the first object file 21*d* is correlated with the "test" type according to the priority order data of the multiple correlation information 301*d* (indicating that the second priority is given to the "test") while the "daily test" type to which the highest priority is given by the multiple correlation information 301*d* is not present in the table 10.

Figure 20:
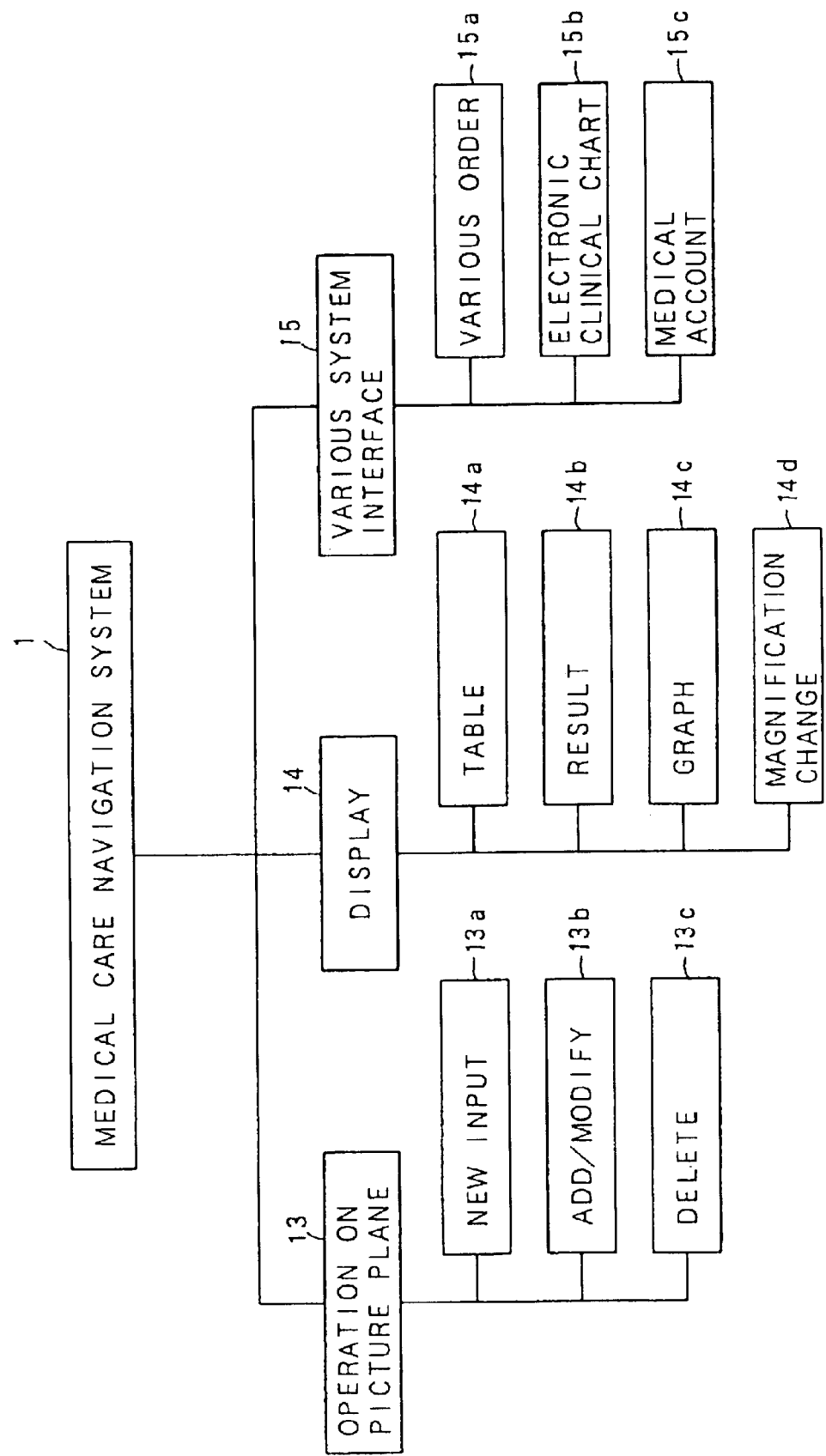
FIG. 20 is a diagram showing functions of the medical care navigation system of the embodiments.

On the other hand, in case that a medical care schedule table 10' shown in a lower right portion of FIG. 20 is currently displayed, i.e., the types "medicine", "workup test" and "daily test" are present in the type column of the medical care schedule table 10', the first object file 21*a* is correlated with the "medicine" type according to the priority order data of the multiple correlation information 301*a*. In this case, the first object file 21*b* is correlated with the "medicine" type according to the priority order data of the multiple correlation information 301*b*. In this case, the first object file 21*c* is correlated with the "workup test" type according to the priority order data of the multiple correlation information 301*c*. Further in this case, the first object file 21*d* is correlated with the "daily test" type according to the priority order data of the multiple correlation information 301*d*.

In this manner, according to the fifth embodiment, it is possible to correlate respective one of the first object files 21*a*, 21*b*, 21*c*, 21*d*, . . . , to the appropriate type on the basis of the multiple correlation information 301*a*, 301*b*, 301*c*, 301*d*, . . . , even in case that the types present in the table are not fixed but are changed in various manners in favor of the medical care schedule and/or record maker such as a doctor.

In addition, if there exists any object file which cannot find to which type the object file itself is to belong, an error message indicating the fact may be outputted. Alternatively, the present embodiment may be constructed such that an operation of automatically re-formatting the table to make a room (i.e., a new type column) for the pertinent object file in the currently displayed table may be performed according to the multiple correlation information of the object files.

Furthermore, the present embodiment may be constructed such that an operation of automatically re-formatting the table to omit or thin out a row for a type, with which any one of the object files is not correlated, in the currently displayed table is performed according to the multiple correlation information 301 (refer to FIG. 15) or the medical care data 211 (refer to FIG. 6) of the first object files 21.

Namely, as shown in an upper portion of FIG. 16, if an empty row exists (i.e., each of the row for the "injection" and the row for the "rehabilitation" is empty) in the table 10, the empty row is thinned out by the automatic re-formatting operation according to the first object file 21, so that a medical care schedule table 10' in which no empty row exists is displayed as shown in a lower portion of FIG. 16. Thus, it is possible to efficiently see the table 10' within a limited vision of the display device.

In the same manner, if an empty column exists in the table 10, the empty column may be thinned out by the automatic re-formatting operation according to the first object file 21, so that the medical care schedule table in which no empty column exists may be displayed.

(VII) Sixth Embodiment

The sixth embodiment of the present invention is explained with reference to FIG. 1, FIG. 2, FIG. 9 and FIG. 17.

The first embodiment is constructed such that the date field (i.e., the absolute date field indicating X year, Y month and Z day) is displayed at the horizontal axis 12 of the table 10 as shown in FIG. 2. In contrast, as shown in FIG. 17, the sixth embodiment has a relative date field 12' using a predetermined reference date (e.g., the day of the operation) as the reference, in parallel to the absolute date field. Then, a portion 202*a* of the relative date field 12' corresponding to the present day at which the present mark 202 is appended (i.e., "AFTER OPE (OPERATION) 14$^{th}$ DAY") is highlight-displayed. Namely, the medical care schedule and/or record system of the sixth embodiment is constructed such that the hardware structure thereof is the same as that of the first embodiment shown in FIG. 1, and the software structure thereof is the same as that of the first embodiment as shown in FIG. 9 except that, in the process of generating the main display data (in the step S3), the main display data is generated to display the relative date field 12' in parallel to the absolute data field according to the format information. Then, after the calculation of the present date and time (in the step S7), a process of locally changing a display luminance, a brightness, a chroma, a display method, a font or the like with respect to the portion 202*a* of the relative date field 12' corresponding to the present day is performed in the process of generating the second sub display data (in the step S8). Other structures of the third embodiment are the same as those of the first embodiment.

(VIII) Seventh Embodiment

The seventh embodiment of the present invention is explained with reference to FIG. 1, FIG. 2, FIG. 9 and FIG. 18.

The first embodiment is constructed such that the date field (i.e., the absolute date field indicating X year, Y month and Z day) is displayed at the horizontal axis 12 of the table 10 as shown in FIG. 2. In contrast, as shown in FIG. 18, the seventh embodiment has a phase field 12", which strides over a plurality of dates and is obtained by dividing one series of medical care term for a certain patient related to the pertinent table into different categories set in advance, in parallel to the absolute date field. Then, a portion 202*b* of the phase field 12" corresponding to the present day at which the present mark 202 is appended (i.e., the phase of "HOSPITALIZATION") is highlight-displayed. Namely, the medical care schedule and/or record system of the seventh embodiment is constructed such that the hardware structure thereof is the same as that of the first embodiment shown in FIG. 1, and the software structure thereof is the same as that of the first embodiment as shown in FIG. 9 except that, in the process of generating the main display data (in the step S3), the main display data is generated to display the phase field 12" in parallel to the absolute data field according to the format information. Then, after the calculation of the present date and time (in the step S7), a process of locally changing a display luminance, a brightness, a chroma, a display method, a font or the like with respect to the portion 202*b* of the phase field 12" corresponding to the present day is performed in the process of generating the second sub display data (in the step S8). The division of the phase field 12" is determined by the external specifying operation through the input device 5 or by referring to the execution timing data 260 and the medical care data 211 in the first object file 21. Other structures of the third embodiment are the same as those of the first embodiment.

(IX) Eighth Embodiment

An eighth embodiment of the present invention is explained with reference to FIG. 19.

Figure 19:
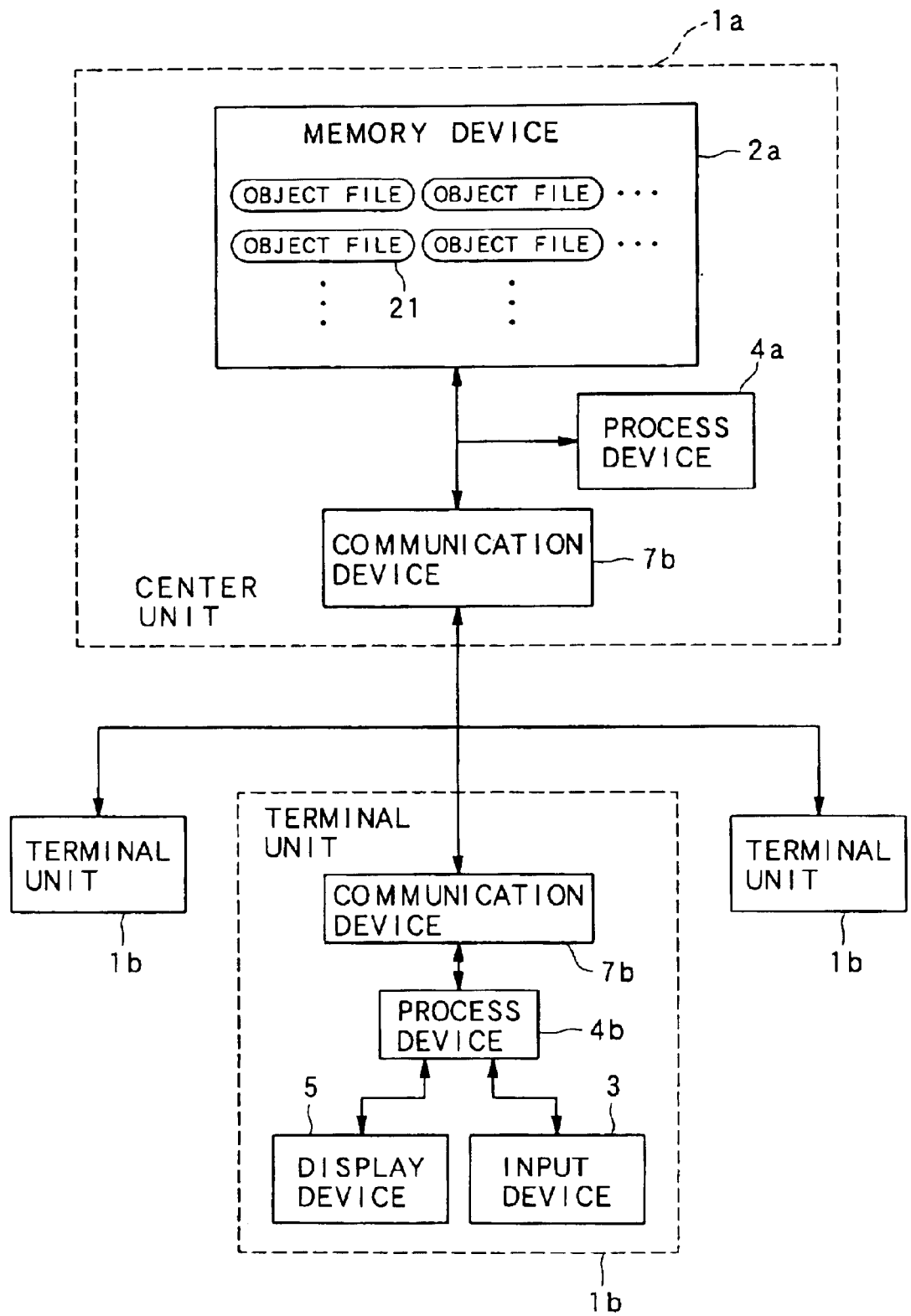
FIG. 19 is a block diagram of a system for aiding to make a medical care schedule and/or record as an eighth embodiment of the present invention.

In FIG. 19, the system for aiding to make the medical care schedule and/or record as the eighth embodiment is provided with a plurality of units communicated through the transmission line. A plurality of first object files 21 are provided on the side of a center unit 1*a*, while the input device 3, the process device 4*a*, the display device 5 and the communication device 7*a* are provided on the side of each terminal unit 1*b*. The center unit 1*a* is provided with: a large size computer, a host computer or a server; and a large size memory device 2*a* for storing the first object files 21. The terminal unit 1*b* is provided with a personal computer, a work station, a mobile computer (i.e., a hand carry type information terminal), an electronic diary or the like. Further, (i) the first object files 21 stored in the memory device 2*a* of the center unit 1*a* and (ii) the input device 3, the process device 4*a* and the display device 5 provided on the terminal unit 1b are coupled through a communication line, which may be a wire-line, a wireless-line, an exclusive line, a general line, a telephone line or the like. Therefore, by virtue of such a structure that the plurality of first object files 21 are stored in the large size memory device 2a equipped on the center unit 1a and that a plurality of terminal units 1b are arranged, it is possible to commonly use the same data by a plurality of terminal units 1b. In such a structure, the process device 4 may be equipped on the center unit 1a or the terminal unit 1b as illustrated by the process devices 4a and 4b. According to the present embodiment, a plurality of object files 21 or data sets stored in the memory device 2a of the center unit 1a can be commonly used, and it is not necessary to equip a large size memory device, which has a capacity enough to store a large number of first object files 21, on each terminal unit 1b, which is advantageous in a practical sense.

(X) Function of System

Finally, the functions of the system for aiding to make the medical care schedule and/or record used in the above described embodiments are conceptually indicated in FIG. 20.

In FIG. 20, the function of the system 1 unifies: a function of "operation on the picture plane" 13 realized by the display device 5, the input device 3 etc. shown in FIG. 1; a function of "display" 14 realized by the display device 5 etc., a function of "various system interface" 15 realized by the communication device 7, the control device 4 etc. The function of "operation on the picture plane" 13 unifies a function of "new input" 13a, a function of "add/modify input" 13b and a function of "delete" 13c. The function of "display" 14 unifies a function of "displaying the table" 14a by use of the medical care data in the predetermined format (refer to FIG. 2 to FIG. 5C and FIG. 10 to FIG. 14), a function of "displaying the result" 14b by use of the medical care data and/or the detail medical data, a function of "displaying the graph" 14c for displaying the graph by use of the detail medical data, and a function of "magnification change" 14d for changing the magnification of picture plane of the display device 5.

Further, the function of "various system interfaces" 15 unifies a function of "various order" 15a for sending an order between each medical care navigation units, a function of "electronic clinical chart" 15b used by the operation unit in medical examination, and a function of "medical account" 15c used in the operation unit for account. The various order function 15a is used in a terminal unit for medicine, which is constructed to graphically-output a medicine list after receiving a medicine order through a communication device from each system interface e.g., from a clinical division. In the present embodiments, on the basis of the order information included in each of the first object files 21 (refer to FIG. 6), it is possible to speedily issue the order corresponding to each medical care action.

The electronic clinical chart function 15b is used in a terminal unit for clinic, which is constructed to graphically-output the clinic chart by use of various data received through the communication device from each system interface. The medical account function 15c is used in a terminal unit for accounting which is constructed to perform a calculation for the medical account by use of various data received through the communication device from each system interface and to graphically-output the medical account book on the basis of the result of calculation.

In this manner, since the functions are unified in the multiple layered structure, each function can be efficiently called and mutual functions organically combined to each other can be performed by the system 1, which is convenient.

As described above in detail, according to each of the present embodiments, a system for aiding to make the medical care schedule and/or record can be realized, which can aid a medical care schedule maker such as a medical doctor etc., to easily and speedily make an appropriate medical care schedule.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

For example, the present invention can be applied to not only a medical care in a hospital but also a medical care in house or home as well as medical care attendance or nursing.

The entire disclosure of Japanese Patent Application No. 11-230880 filed on Aug. 17, 1999 including the specification, claims, drawings and summary is incorporated herein by reference in its entirety.

What is claimed is:

1. A system for aiding to make a medical care schedule and/or record comprising:

a plurality of files for respectively including medical care data indicating one of a plurality of types of medical care actions, which are set in advance, in correlation with execution timing data indicating an execution timing of respective one of the medical care actions;

a date and time measuring device for measuring a present date and time;

a display controlling device for (i) generating main display data to display the medical care data composing one series of medical care schedule for one patient in a format of a table, in which the medical care data is arranged in first rows for each type of the medical care actions and in second rows orthogonal to said first rows for each date, on the basis of the medical care data and the execution timing data included in said files, (ii) selecting one of a plurality of kinds of condition marks set in advance, in correspondence with a relationship between the execution timing of the respective one of the medical care actions and the measured present date and time, (iii) generating first sub display data to display the selected condition mark superimposed on or at the vicinity of the medical care data corresponding to the selected condition mark in the table, (iv) calculating a present position in the table corresponding to the measured present date and time under a condition that a width of one day of the table is converted into 24 hours, and (v) generating second sub display data to display a present mark at the calculated present position; and a display device for displaying the medical care data in the format of the table together with the condition mark and the present mark on the basis of the main display data, the first sub display data and the second sub display data, wherein each of said files comprises a first object file for including the medical care data and the execution timing data and further including procedure information, in accordance with which said display controlling device selects one of the condition marks and generates the first sub display data, and said display controlling device generates the first sub display data to display the condition mark in one kind if a time interval from the execution timing of the respective one of the medical care actions to the present date and time is longer than a predetermined interval set in advance, generates the first sub display data to display the condition mark in another kind if the time interval is not longer than the predetermined interval, and generates the first sub display data to display the condition mark in further another kind if the present date and time has passed through the execution timing and the respective one of the medical care actions was not completed.

2. A system according to claim 1, wherein said first object file further includes procedure information, in accordance with which said display controlling device generates the main display data to display the medical care data in respective cells in the table.

3. A system according to claim 1, further comprising a second object file for including procedure information, in accordance with which said display controlling device calculates the present position and generates the second sub display data.

4. A system according to claim 1, wherein said display controlling device generates the first sub display data to display the condition mark, which extends along the second rows for each date of the table in a length corresponding to a predetermined time duration, if the medical care action corresponding to the condition mark is continuously executed for the predetermined time duration.

5. A system according to claim 1, wherein said display controlling device selects one of the condition marks differently in accordance with information indicating whether or not the respective one of the medical care actions has been already performed.

6. A system according to claim 1, wherein said display controlling device selects one of the condition marks differently in accordance with information indicating whether or not an order for the respective one of the medical care actions has been already issued.

7. A system according to claim 1, wherein said display controlling device generates the first sub display data to display the condition mark at a position, which corresponds to the execution timing of the respective one of the medical care actions under the condition that the width of one day of the table is converted into 24 hours, in the table.

8. A system according to claim 1, wherein said display controlling device generates the second sub display data to display a line shaped mark, which strides over a plurality of cells corresponding to a same day of the table, as the present mark.

9. A system according to claim 1, further comprising an input device for inputting the medical care data and the execution timing data to said files,
said display controlling device generating the main display data and generating the first sub display data and the second sub display data by referring to the measured data and time, each time when the medical care data and the execution timing data are inputted by said input device.

10. A system according to claim 1, wherein said display controlling device generates the first sub display data and the second sub display data by periodically referring to the measured data and time.

11. A system according to claim 1, wherein
the format of the table has a relative date field using a predetermined reference date as a reference in parallel to an absolute date field, and
said display controlling device highlight-displays a portion of the relative date field, which correspondence to the measured present date and time.

12. A system according to claim 1, wherein
the format of the table has a phase field, which strides over a plurality of dates and is obtained by dividing one series of medical care term for said one patient into different categories set in advance, in parallel to an absolute date field, and
said display controlling device highlight-displays a portion of the phase field, which corresponds to the measured present date and time.

13. A system according to claim 1, wherein the format of the table is such a format that each cell is prescribed for respective one of large categories of the medical care actions and that a plurality of the medical care data of a plurality of small categories belonging to one large category are arranged within one cell,
said display controlling device generates the main display data to display a plurality of the medical care data of one small category such that the plurality of the medical care data are arranged in one row and stride over a plurality of cells corresponding to said one large category.

14. A system according to claim 1, wherein
the format of the table is such a format that each cell is prescribed for respective one of large categories of the medical care actions and that a plurality of the medical care data of a plurality of small categories belonging to one large category are arranged within one cell, and
said display controlling device generates the main display data such that a plurality of the medical care data of one small category are arranged in parallel to each other within one cell if a width of a date field of the table is smaller than a predetermined width and that a plurality of the medical care data of one small category are arranged in serial to each other within one cell if the width of the date field is larger than the predetermined width.

15. A system according to claim 1, further comprising a specification device for specifying a width of a date field of the table,
said display controlling device generating the first sub data and the second sub data by referring to the measured present date and time each time when the width of the date field is changed by said specifying device.

16. A system according to claim 15, wherein said display controlling device generates the main display data to display at least one portion of the medical care data by an information amount set in advance in correspondence with the specified width when the width of the date field is specified by the specifying device.

17. A system according to claim 1, wherein
each of said files further includes multiple correlation information, which correlates the medical care data with one or a plurality of type fields for the types of the medical care actions of the table while appending a priority order to the medical care data, and
said display controlling device selects one of the type fields, to which the medical care data belongs, in accordance with the multiple correlation information and generates the main display data to display the medical care data in the cell corresponding to the selected type field.

18. A system according to claim 1, wherein said display controlling device generates the main display data to thin out a type field for the type of the medical care action of the table, which does not correspond to any medical care data to be displayed in the table, from the table.

19. A system according to claim 1, wherein said display controlling device generates the main display data to thin out a date field of the table, which does not correspond to any execution timing data, from the table.

20. A system according to claim 1, wherein
said system comprises two units communicated to each other through a communication line, wherein
said files are provided in one of the two units, and
said display device is provided in another of the two units.

21. A system according to claim 1, wherein
each of said files includes setting procedure information to set at least relative execution timings of the medical care actions composing one series of medical care schedule respectively, in addition to the medical care data and the execution timing data, and
in case that the medical care actions composing one series of medical care schedule are specified, said display controlling device sets the execution timings of the specified medical care action in accordance with the setting procedure information included in said files including the medical care data indicating the specified medical care actions respectively, to thereby update the execution timing data.

22. A program storage device readable by a system for aiding to make a medical care schedule and/or record, tangibly embodying a program of instructions executable by said system to perform method processes for aiding to make a medical care schedule and/or record, said system comprising (i) a plurality of files for respectively including medical care data indicating one of a plurality of types of medical care actions, which are set in advance, in correlation with execution timing data indicating an execution timing of respective one of the medical care actions, and (ii) a date and time measuring device for measuring a present date and time,
said method processes comprising the processes of:
generating main display data to display the medical care data composing one series of medical care schedule for one patient in a format of a table, in which the medical care data is arranged in first rows for each type of the medical care actions and in second rows orthogonal to said first rows for each date, on the basis of the medical care data and the execution timing data included in said files;
selecting one of a plurality of kinds of condition marks set in advance, in correspondence with a relationship between the execution timing of the respective one of the medical care actions and the measured present date and time;
generating first sub display data to display the selected condition mark superimposed on or at the vicinity of the medical care data corresponding to the selected condition mark in the table;
calculating a present position in the table, corresponding to the measured present date and time under a condition that a width of one day of the table is converted into 24 hours;
generating second sub display data to display a present mark at the calculated present position; and
displaying the medical care data in the format of the table together with the condition mark and the present mark on the basis of the main display data, the first sub display data and the second sub display data, wherein
each of said files comprises a first object file for including the medical care data and the execution timing data and further including procedure information, in accordance with which said display controlling device selects one of the condition marks and generates the first sub display data, and
said display controlling device generates the first sub display data to display the condition mark in one kind if a time interval from the execution timing of the respective one of the medical care actions to the present date and time is longer than a predetermined interval set in advance, generates the first sub display data to display the condition mark in another kind if the time interval is not longer then the predetermined interval, and generates the first sub display data to display the condition mark in further another kind if the present date and time has gassed through the execution timing and the respective one of the medical care actions has not been completed.

23. A computer data signal embodied in a carrier wave and representing a series of instructions which cause a computer to perform processes for aiding to make a medical care schedule and/or record in a system for aiding to make the medical care schedule and/or record, said system comprising (i) a plurality of files for respectively including medical care data indicating one of a plurality of types of medical care actions, which are set in advance, in correlation with execution timing data indicating an execution timing of respective one of the medical care actions and (ii) a date and time measuring device for measuring a present date and time,
said method processes comprising the processes of:
generating main display data to display the medical care data composing one series of medical care schedule for one patient in a format of a table, in which the medical care data is arranged in first rows for each type of the medical care actions and in second rows orthogonal to said first rows for each date, on the basis of the medical care data and the execution timing data included in said files;
selecting one of a plurality of kinds of condition marks set in advance, in correspondence with a relationship between the execution timing of the respective one of the medical care actions and the measured present date and time;
generating first sub display data to display the selected condition mark superimposed on or at the vicinity of the medical care data corresponding to the selected condition mark in the table;
calculating a present position in the table corresponding to the measured present date and time under a condition that a width of one day of the table is converted into 24 hours;
generating second sub display data to display a present mark at the calculated present position; and
displaying the medical care data in the format of the table together with the condition mark and the present mark on the basis of the main display data, the first sub display data and the second sub display data, wherein
each of said files comprises a first object file for including the medical care data and the execution timing data and further including procedure information, in accordance with which said display controlling device selects one of the condition marks and generates the first sub display data, and said display controlling device generates the first sub display data to display the condition mark in one kind if a time interval from the execution timing of the respective one of the medical care actions to the present date and time is longer than a predetermined interval set in advance, generates the first sub display data to display the condition mark in another kind if the time interval is not longer than the predetermined interval, and generates the first sub display data to display the condition mark in further another kind if the present date and time has passed through the execution timing and the respective one of the medical care actions has not been completed.

* * * * *